(12) United States Patent
Teramura et al.

(10) Patent No.: US 7,830,524 B2
(45) Date of Patent: *Nov. 9, 2010

(54) OPTICAL TOMOGRAPH USING A PLURALITY OF WAVELENGTH-SWEPT LIGHT BEAMS

(75) Inventors: Yuichi Teramura, Ashigarakami-gun (JP); Sadato Akahori, Ashigarakami-gun (JP); Karin Kuroiwa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 195 days.

This patent is subject to a terminal disclaimer.

(21) Appl. No.: 11/941,601

(22) Filed: Nov. 16, 2007

(65) Prior Publication Data

US 2008/0117427 A1 May 22, 2008

(30) Foreign Application Priority Data

Nov. 17, 2006 (JP) .............................. 2006-311286

(51) Int. Cl.
*G01B 9/02* (2006.01)
(52) U.S. Cl. ..................................... 356/477; 356/479
(58) Field of Classification Search .................. 356/477, 356/479, 497
See application file for complete search history.

(56) References Cited

U.S. PATENT DOCUMENTS

| | | | |
|---|---|---|---|
| 5,321,501 A * | 6/1994 | Swanson et al. | 356/479 |
| 5,459,570 A * | 10/1995 | Swanson et al. | 356/479 |
| 5,892,583 A * | 4/1999 | Li | 356/479 |
| 6,665,320 B1 | 12/2003 | Arbore et al. | |
| 7,538,884 B2 * | 5/2009 | Teramura et al. | 356/489 |
| 7,545,504 B2 * | 6/2009 | Buckland et al. | 356/479 |
| 2004/0239938 A1 * | 12/2004 | Izatt | 356/450 |
| 2007/0024856 A1 * | 2/2007 | Izatt et al. | 356/497 |

FOREIGN PATENT DOCUMENTS

| | | |
|---|---|---|
| JP | 2001-264246 A | 9/2001 |
| JP | 2006-047264 A | 9/2001 |
| JP | 2002-214125 A | 7/2002 |

OTHER PUBLICATIONS

Choma et al, Sensitivity advantages of swept source and Fourier domain optical coherence tomography, Optics Express Sep. 2003, vol. 11, No. 18, pp. 2183-2189.*
Mitsuo Takeda, "Optical Frequency Scanning Interference Microscopes", Optics Engineering Contact, 2003, pp. 426-432, vol. 41, No. 7.

* cited by examiner

*Primary Examiner*—Samuel A Turner
(74) *Attorney, Agent, or Firm*—Sughrue Mion, PLLC

(57) ABSTRACT

An optical tomograph is equipped with: a light source unit for emitting a plurality of light beams, the wavelengths of which are swept within different predetermined wavelength bands respectively with the same period; light divider which divides each light beam into a measuring light beam and a reference light beam; light beam combiner which combines reflected light beams, which are the measuring light beams reflected by a measurement target when the measuring light beams are irradiated thereon, with a reference light. An interference light detector detects an interference light beam, which is formed by the reflected light beam and the reference light combined by the light beam combiner, for each of the light beams as an interference signal. A tomographic image processor generates a tomographic image of the measurement target employing the plurality of interference signals detected by the interference light detector.

5 Claims, 16 Drawing Sheets

FIG.6
INTERMEDIATE
TOMOGRAPHIC
DATA $r_a$
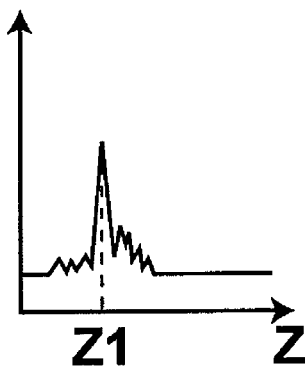
INTERMEDIATE
TOMOGRAPHIC
DATA $r_b$
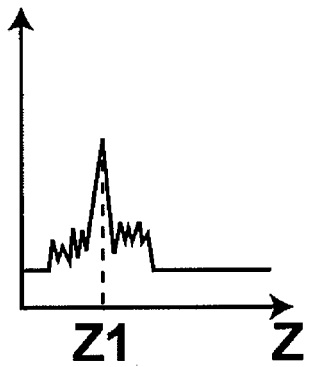
TOMOGRAPHIC
DATA $r$
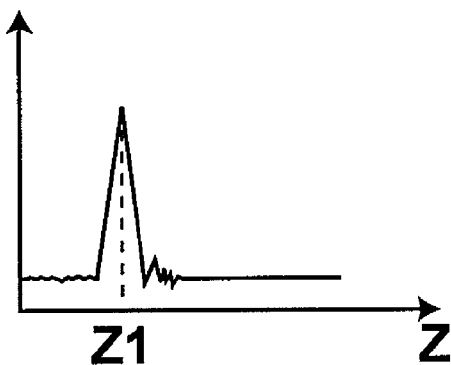

OPTICAL TOMOGRAPH USING A PLURALITY OF WAVELENGTH-SWEPT LIGHT BEAMS

BACKGROUND OF THE INVENTION

1. Field of the Invention

The present invention relates to an optical tomograph that obtains optical tomographic images by OCT (Optical Coherence Tomography) measurement.

2. Description of the Related Art

Conventionally, optical tomographs that utilize OCT measurement are used to obtain optical tomographic images of living tissue. In these optical tomographs, a low coherence light beam emitted from a light source is divided in to a measuring light beam and a reference light beam. Thereafter, a reflected light beam, which is the measuring light beam reflected or backscattered by a measurement target when the measuring light beam is irradiated onto the measurement target, is combined with the reference light beam. Tomographic images are obtained, based on the intensity of a coherent light beam obtained by combining the reflected light beam and the reference light beam. Hereinafter, the light beam, which is reflected or backscattered by the measurement target, will be collectively referred to as a "reference light beam".

OCT measurement can be roughly divided into two types, TD-OCT (Time Domain Optical Coherence Tomography) and FD-OCT (Fourier Domain Optical Coherence Tomography). In TD-OCT measurement, the intensity of the interference light beam is measured while changing the optical path length of the reference light beam. Thereby, intensity distributions of the reflected light beam corresponding to measuring positions in the depth direction of the measurement target (hereinafter, referred to as "depth positions") are obtained.

On the other hand, in FD-OCT measurement, the optical path lengths of the reference light beam and the signal light beam are not changed. The intensity of the interference light beam is measured for each spectral component thereof, and frequency analysis, such as Fourier transform, is administered on the obtained spectral interference intensity signals. Thereby, intensity distributions of the reflected light beam corresponding to the depth positions of the measurement target are obtained. FD-OCT measurement has been gathering attention recently as a method that enables high speed measurement, due to the mechanical scanning associated with TD-OCT measurement being obviated.

Optical tomographs that perform SD-OCT (Spectral Domain Optical Coherence Tomography) measurement and optical tomographs that perform SS-OCT (Swept Source Optical Coherence Tomography) measurement are two types of optical tomographs that employ FD-OCT measurement. In an SD-OCT optical tomograph, a wide band low coherence light beam is emitted from an SLD (Super Luminescent Diode), an ASE (Amplified Spontaneous Emission) light source, or a white light source. The wide band low coherence light beam is divided into a measuring light beam and a reference light beam by a Michelson interferometer or the like. Thereafter, the measuring light beam is irradiated onto a measurement target, and a reflected light beam reflected by the measurement target is caused to interfere with the reference light beam. The interference light beam formed thereby is spectrally decomposed into each frequency component by a spectrometer, and the intensity of each frequency component of the interference light beam is measured by a detector array, in which elements such as photodiodes are provided in an array. A computer administers Fourier transform on the obtained spectral interference intensity signals, to obtain a tomographic image.

Meanwhile, an SS-OCT optical tomographs utilizes a light source that periodically sweeps the frequency of a laser beam. Reflected light beams of each wavelength are caused to interfere with reference light beams of each wavelength. Temporal waveforms of signals corresponding to the temporal variations in the frequency of the laser beam are measured, and a computer administers Fourier transform on the obtained spectral interference intensity signals, to obtain a tomographic image.

In order to obtain higher resolution and higher image quality tomographic images with an OCT apparatus, it is necessary for the wavelength band of light emitted by a light source to be wide, and to increase data points corresponding to the wide wavelength band. However, SD-OCT apparatuses commonly detect each wavelength of interference light beams with detector arrays, in which elements such as photodiodes are provided in an array. Therefore, the number of data points is limited by the number of elements provided in the detector array. If the number of elements of the detector array is to be increased in order to increase the number of data points, cost increases, productivity decreases, and measurement rates deteriorate, which is not favorable. In contrast, the number of data points can be increased in SS-OCT apparatuses by increasing the sampling frequency of a circuit that converts photoelectric current from a detector to digital values, assuming that the frequency sweeping period of the light source is constant. Therefore, the number of data points can be increased at low cost, while maintaining measurement rates in SS-OCT apparatuses.

In each type of OCT measurement described above, it is known that the use of a measuring light beam having a wide spectral width improves spatial resolution (refer to Japanese Unexamined Patent Publication No. 2002-214125). Japanese Unexamined Patent Publication No. 2002-214125 discloses a method for widening the spectral width of a measuring light beam, in which a plurality of light sources that each emit light beams having a different spectral band are used, and an optical integrator integrates the light beams emitted from the plurality of light sources, to obtain a single light beam.

With respect to SD-OCT measurement, Japanese Unexamined Patent Publication No. 2001-264246 discloses a method in which light beams, which are emitted by a plurality of gain media that have overlapping wavelength bands, are combined to form a continuous spectrum. With respect to SS-OCT measurement, Japanese Unexamined Patent Publication No. 2006-047264 discloses a configuration in which light beams emitted from a plurality of wavelength scanning light sources (each constituted by a gain medium and a wavelength selecting element) are combined. As another example, U.S. Pat. No. 6,665,320 discloses a configuration in which light beams emitted from a plurality of gain media are combined, and a single wavelength selecting element controls the plurality of gain media.

As described above, light beams emitted from a plurality of light sources are combined in order to obtain high spatial resolution. However, if the plurality of light beams having different wavelengths are simultaneously irradiated onto a measurement target, the interference data becomes mixed and undetectable, because the detector is constituted by single elements in conventional SS-OCT apparatuses.

For this reason, the apparatuses disclosed in Japanese Unexamined Patent Publication No. 2006-042764 and U.S. Pat. No. 6,665,320 are configured such that a light beam that enters a detector at a given time is of a single wavelength by controlling the light source or by providing switching elements. This configuration enables the use of a wide band measuring light beam, but it takes time to irradiate all of the wavelength bands of the measuring light beam, and as a result, a problem arises that the measurement rate decreases.

SUMMARY OF THE INVENTION

The present invention has been developed in view of the foregoing circumstances. It is an object of the present invention to provide an optical tomograph which is capable of obtaining high resolution tomographic images at high speeds.

An optical tomograph of the present invention comprises:

a light source unit for emitting a plurality of light beams, the wavelengths of each of which are periodically swept within different predetermined wavelength bands respectively;

light dividing means, for dividing each of the light beams emitted from the light source unit into a measuring light beam and a reference light beam;

combining means, for combining reflected light beams, which are the measuring light beams reflected by a measurement target when the measuring light beams are irradiated thereon, with the reference light beams divided by the light dividing means;

interference light detecting means, for detecting an interference light beam, which is formed by the reflected light beam and the reference light beam being combined by the combining means, for each of the light beams as an interference signal; and tomographic image processing means, for generating a tomographic image of the measurement target employing the plurality of interference signals detected by the interference light detecting means.

Here, the light source unit maybe of any construction as long as it emits a plurality of light beams. For example, the light source unit may be constituted by single light source that emits a plurality of light beams, or by a plurality of wavelength variable light sources.

Note that the wavelength bands of each light beam may be discrete, or may overlap each other. The plurality of light beams emitted from the light source unit may form a continuous spectrum or a discontinuous spectrum. The widths of the wavelength bands of each light beam may or may not be uniform.

Note that it is preferable for the same number of interference light detecting means to be provided as the number of light beams, such that the interference light beam corresponding to each light beam can be detected separately.

The optical tomograph of the present invention may be configured such that: at least two of the plurality of light beams emitted from the light source unit have discrete wavelength bands and continuous spectra within their respective wavelength bands; and the tomographic image processing means generates a tomographic image of a single portion of the measurement target, employing the interference signals obtained from the at least two light beams.

Alternatively, the optical tomograph of the present invention may be configured such that: at least two of the plurality of light beams emitted from the light source unit have wavelength bands that overlap; and an optical filter for shielding light of the overlapping wavelength band is provided in the optical path between the light source unit and the interference light detecting means.

As a further alternative, the optical tomograph of the present invention may be configured such that: at least two of the plurality of light beams emitted from the light source unit have wavelength bands that overlap; and the tomographic image processing means removes interference signals obtained based on the light of the overlapping wavelength band.

The optical tomograph of the present invention may comprise: a separate light dividing means and a separate combining means are provided for each of the light beams emitted from the light source unit.

Note that in the present specification, the term "discrete wavelength bands" refers to the wavelength bands of two light beams having a wavelength band having a light intensity of approximately −10 db with respect to the peak wavelengths of the two light beams. That is, "discrete wavelength bands" refer to wavelength bands having a wavelength band having an intensity too low to contribute to OCT measurement therebetween. In the case that the peak intensities of the two light beams are different, the lower peak intensity is employed to calculate the difference between the peak intensity and the low intensity wavelength band. The phrase "wavelength bands that overlap" refers to the opposite of the above.

Similarly, the term "discontinuous spectrum" refers to the spectrum of a light beam, in which a low intensity wavelength band having an intensity of approximately −10 db with respect to the peak intensity of the light beam, is present within a wavelength band sufficiently greater than a frequency band sampling interval, which is measured in FD-OCT measurement. That is, the "discontinuous spectrum" is a spectrum in which there are wavelength bands having an intensity too low to contribute to OCT measurement, within a wavelength band sufficiently greater than the frequency band sampling interval. The term "continuous spectrum" refers to the opposite of the above. Note that in light beams such as those emitted by semiconductor lasers, in which the frequency are modulated in a stepped manner, and those emitted by light sources that employ frequency combs to emit light beams having wide bands of densely arranged linear spectra, the intervals between the discrete wavelength bands are equal to or narrower than the frequency sampling intervals measured in FD-OCT measurement. Therefore, such light beams are considered to have continuous spectra.

In the present specification, the term "spectrum" refers not to an instantaneous spectrum, but the distribution of light intensities with respect to wavelengths over the entire time that the light beams are being emitted, unless otherwise noted.

The optical tomograph of the present invention comprises: a light source unit for emitting a plurality of light beams, the wavelengths of each of which are periodically swept within different predetermined wavelength bands respectively; and a plurality of interference light detecting means, each for detecting an interference light beam corresponding to each of the plurality of light beams as an interference signal. Therefore, when the plurality of light beams having different wavelengths are simultaneously irradiated on the measurement target, the interference light beams generated thereby do not mix with each other, and the plurality of interference signals corresponding to each light beam can be obtained simultaneously. Accordingly, the measurement rate can be improved compared to conventional tomographs, and high resolution tomographic images can be obtained at high speed. It is necessary to synchronize and control the light source units of conventional optical tomographs to limit the wavelength of a light beam that enters a detector. However, the optical tomograph of the present invention obviates such control, and the apparatus can be simplified. In addition, each of the interference light detecting means can be of a specialized structure for detecting the interference light beam corresponding to the wavelength band of each light beam. Therefore, the detection accuracy of the interference light detecting means can be improved, thereby improving the resolution of the tomographic image. Further, the need for the components to be employed in the interference light detecting means to detect a wide band light beam is obviated, ad it is only necessary for the components to be capable of detecting the specific wavelength band of each light beam. Accordingly, the constraints placed on the optical tomograph are lessened compared to conventional optical tomographs, general purpose components can be employed, and the structure of the apparatus can be simplified.

The optical tomograph of the present invention may be configured such that: at least two of the plurality of light beams emitted from the light source unit have discrete wavelength bands and continuous spectra within their respective wavelength bands; and the tomographic image processing means generates a tomographic image of a single portion of the measurement target, employing the interference signals obtained from the at least two light beams. In this case, tomographic images having high image quality equivalent to those obtained by wide band light sources having continuous spectra, or by combinations of light sources that form a continuous spectrum over a wide band can be obtained employing interference signals obtained from a plurality of light beams emitted from the light source unit having a simple structure.

The optical tomograph of the present invention may be configured such that: at least two of the plurality of light beams emitted from the light source unit have wavelength bands that overlap; and an optical filter for shielding light of the overlapping wavelength band is provided in the optical path between the light source unit and the interference light detecting means. In this case, the plurality of interference light beams corresponding to the light beams having the overlapping wavelength bands can be positively separated and detected.

The optical tomograph of the present invention may be configured such that: at least two of the plurality of light beams emitted from the light source unit have wavelength bands that overlap; and the tomographic image processing means removes interference signals obtained based on the light of the overlapping wavelength band. In this case, the plurality of interference light beams corresponding to the light beams having the overlapping wavelength bands can be positively separated.

The optical tomograph of the present invention may comprise: a separate light dividing means and a separate combining means are provided for each of the light beams emitted from the light source unit. In this case, the light dividing means and the combining means can be optimized for the wavelength band of each of the light beams, and the resolution of obtained tomographic images can be improved. Further, the need for the components to be employed in the light dividing means and the combining means handle a wide band light beam is obviated, ad it is only necessary for the components to be capable of handling the specific wavelength band of each light beam. Accordingly, the constraints placed on the optical tomograph are lessened compared to conventional optical tomographs, general purpose components can be employed, and the structure of the apparatus can be simplified.

BRIEF DESCRIPTION OF THE DRAWINGS

FIG. 6 is a diagram that illustrates the method by which tomographic data is generated from a plurality of pieces of intermediate tomographic data, by the tomographic image processing means of FIG. 1.

BEST MODE FOR CARRYING OUT THE INVENTION

Figure 1:
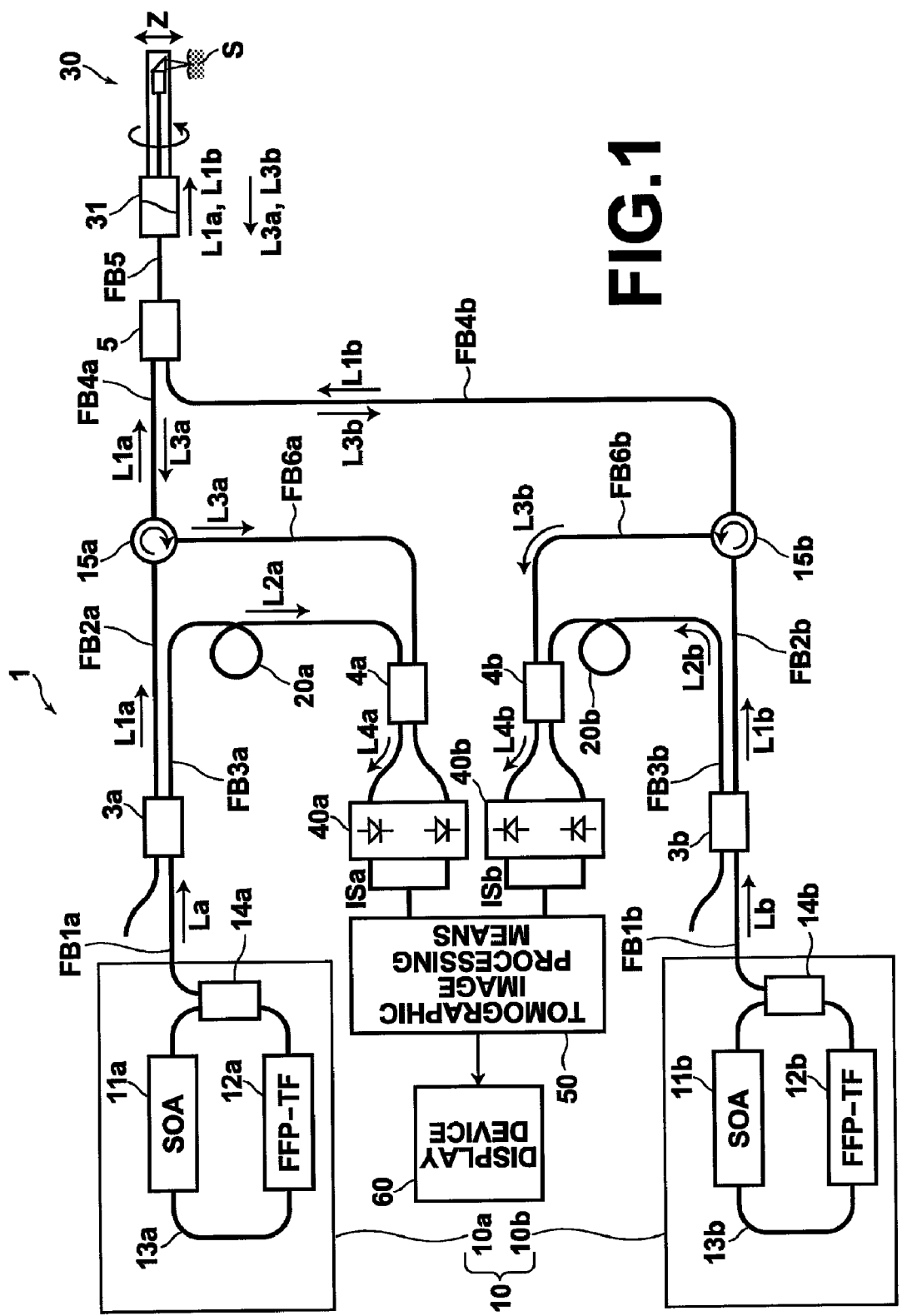
FIG. 1 is a diagram that illustrates the schematic construction of an optical tomograph according to a first embodiment of the present invention.

Hereinafter, optical tomographs according to preferred embodiments of the present invention will be described in detail with reference to the attached drawings. FIG. 1 is a diagram that illustrates the schematic construction of an optical tomograph 1 according to a first embodiment of the present invention. The optical tomograph 1 obtains tomographic images of measurement targets such as tissue within body cavities or cells by SS-OCT measurement, using a Mach-Zehnder type interferometer.

The optical tomograph 1 comprises: a light source unit 10 for emitting light beams La and Lb, the wavelengths of each of which are periodically swept within different predetermined wavelength bands respectively; light dividing means 3a and 3b for respectively dividing the light beams La and Lb into measuring light beams L1a, L1b and reference light beams L2a, L2b; combining means 4a and 4b for combining reflected light beams L3a, L3b, which are the measuring light beams L1a and L1b reflected by a measurement target S when irradiated thereon, with the reference light beams L2a, L2b; an interference light detecting means 40a, for detecting an interference light beam L4a, which is formed by the combining means 4a combining the reflected light beam L3a with the reference light beam L2a as interference signals ISa; an interference light detecting means 40a, for detecting an interference light beam L4b, which is formed by the combining means 4b combining the reflected light beam L3b with the reference light beam L2b as interference signals ISb; and a tomographic image processing means 50, for detecting tomographic data (reflectance) regarding various depth positions of the measurement target S employing the interference signals ISa and ISb, to obtain a tomographic image of the measurement target S. The interference light detecting means 40a and 40b detect the interference light beams L4a and L4b corresponding to each of the light beams La and Lb.

Note that the measuring light beam L1a, the reference light beam L2a, the reflected light beam L3a, and the interference light beam L4a are based on the light beam La, and are light beams of the same wavelength band as the light beam La. Similarly, the measuring light beam L1b, the reference light beam L2b, the reflected light beam L3b, and the interference light beam L4b are based on the light beam Lb, and are light beams of the same wavelength band as the light beam Lb. Here, "corresponding to each of the light beams" means corresponding to each wavelength band.

The light source unit 10 comprises two wavelength sweeping light sources 10a and 10b that emit laser beams L while sweeping the frequencies (wavelengths) thereof within a predetermined period. The light source 10a comprises: a semiconductor optical amplifier 11a (hereinafter, simply referred to as "SOA") as a gain medium; a wavelength selecting means 12a constituted by an FFP-TF (Fiber Fabry Perot Tunable Filter); and an optical fiber FB13a which is connected to both ends of the SOA 11a and the wavelength selecting means 12a, to form an annular resonator.

The SOA 11a functions to emit a slight amount of light into the optical fiber FB13a connected to a first end thereof, when a drive current is injected thereinto, and to amplify the light that enters a second end thereof from the optical fiber FB13a. The SOA 11a is constituted by an InGaAs/AlGaAs element that has a light emission wavelength band from 1000 nm to 1100 nm, for example. The SOA 11a causes a laser beam to oscillate within the annular resonator. The laser beam is divided by an optical coupler 14a, which is connected to the optical fiber 13a and which has a division ratio of 10:90. The laser beam propagates through an optical fiber FB1a, and is emitted as the light beam La.

The wavelength selecting means 12a is configured such that the wavelength of light transmitted therethrough is variable. The wavelength selecting means 12a selects wavelengths to be emitted from the laser beam that oscillates within the annular resonator, such that the wavelength of the emitted light beam La is swept within the predetermined period.

The light source 10b is of a similar construction as the light source 10a, and comprises: a semiconductor optical amplifier 11b as a gain medium; a wavelength selecting means 12b constituted by an FFP-TF; and an optical fiber FB13b which is connected to both ends of the SOA 11b and the wavelength selecting means 12b, to form an annular resonator. The SOA 11b is constituted by an InGaAsP element that has a light emission wavelength band from 1250 nm to 1350 nm, for example. The SOA 11b causes a laser beam to oscillate within the annular resonator. The laser beam is divided by an optical coupler 14b, which is connected to the optical fiber 13b and which has a division ratio of 10:90. The laser beam propagates through an optical fiber FB1b, and is emitted as the light beam Lb. The wavelength selecting means 12b of the light source 10b also performs wavelength selection, such that the wavelength of the emitted light beam Lb is swept within the predetermined period.

Figure 2A:
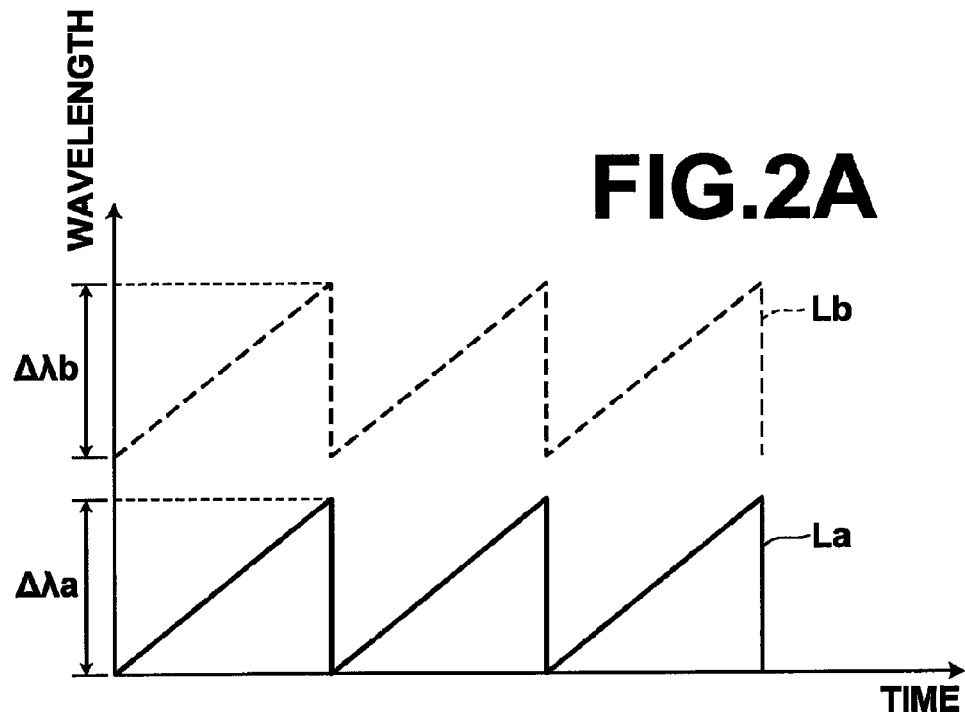
FIG. 2A is a graph that illustrates the manner in which the wavelengths of light beams emitted by the light source unit of FIG. 1 are swept.
Figure 2B:
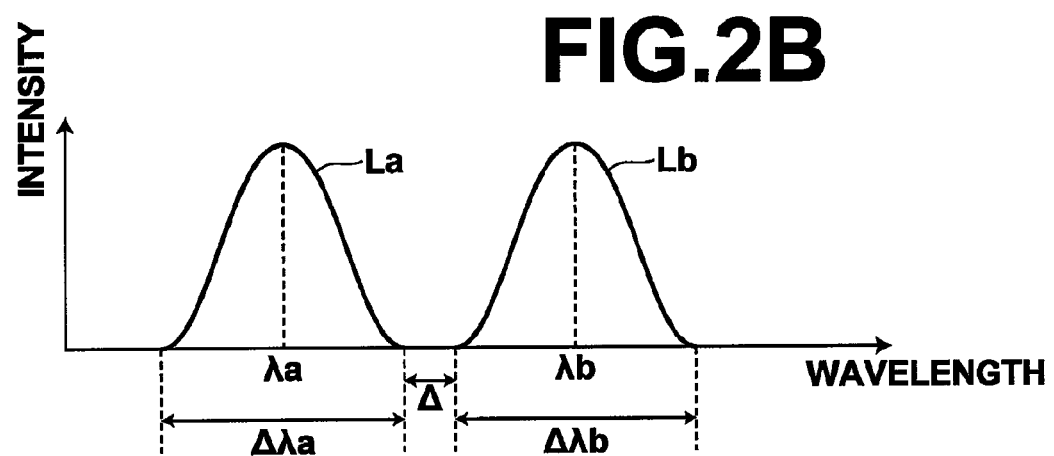
FIG. 2B is a graph that illustrates the spectra of the light beams emitted by the light source unit of FIG. 1.

FIG. 2A is a graph that illustrates an example of the manner in which the wavelengths of the light beams La and Lb emitted by the light sources 10a and 10b are swept. FIG. 2B is a graph that illustrates examples of the spectra of the light beams La and Lb emitted by the light sources 10a and 10b. The light source 10a emits the light beam La, the wavelength of which is swept within a wavelength band $\Delta\lambda a$ at a predetermined period, and the light source 10b emits the light beam Lb, the wavelength of which is swept within a wavelength band $\Delta\lambda b$ at the same period. The light beams La and Lb have continuous spectra within their respective wavelength bands $\Delta\lambda a$ and $\Delta\lambda b$, and the wavelength bands $\Delta\lambda a$ and $\Delta\lambda b$ are discrete from each other. Thereby, the spectrum formed by the light beams La and Lb emitted by the light source unit 10 is discontinuous.

Note that here, the phrase "the wavelength bands $\Delta\lambda a$ and $\Delta\lambda b$ are discrete" refers to a state in which a wavelength band having a light intensity of approximately −10 db with respect to the peak wavelengths $\lambda a$ and $\lambda b$ of the two light beams La and Lb is present between the peak wavelengths $\lambda a$ and $\lambda b$, as illustrated in FIG. 2B. In the present embodiment, $\Delta\lambda a$ is a wavelength band from 1000 nm to 1100 nm, and $\Delta\lambda b$ is a wavelength band from 1250 nm to 1350 nm. Therefore, there is a region from 1100 nm to 1250 nm, at which no light is emitted.

The light dividing means 3a and 3b of FIG. 1 are constituted by 2×2 optical fiber couplers with division ratios of 90:10, for example. The light dividing means 3a functions to divide the light beam La into the measuring light beam L1a and the reference light beam L2a. The light dividing means 3b functions to divide the light beam Lb into the measuring light beam L1b and the reference light beam L2b. The division ratio of the light dividing means 3a and 3b is measuring light beam:reference light beam=90:10.

A probe 30 guides the measuring light beams L1a and L1b onto the measurement targets. The measuring light beams L1a and L1b enter the probe 30 via an optical rotary connector 31, are guided to the measurement target S, and are simultaneously emitted onto the same portion of the measurement target S. The reflected light beams L3a and L3b, which are reflected by the measurement target S, are also guided through the probe 30. A fiber portion of the probe 30 beyond the rotary optical connector 31 is configured to be rotated by a motor (not shown), and thereby, the light beams are scanned in a circumferential direction. This scanning enables obtainment of two dimensional tomographic images. Further, a motor (not shown) is configured to scan the distal end of the probe 30 in a direction perpendicular to the plane formed by the scanning circle of the optical path of the measuring light beams L1a and L1b. Thereby, obtainment of three dimensional tomographic images is also enabled. In addition, the probe 30 is removably mounted to an optical fiber FB5 via an optical connector (not shown). Of course, the shape of the distal end of the probe 30 and the scanning method are not limited to those described above. Alternatively, two dimensional scanning may be realized by providing a high speed scanning mirror at the distal end of the probe 30, for example.

A combining/dividing means 5 is provided in the optical path between the light dividing means 3a and the probe 30, and in the optical path between the light dividing means 3b and the probe 30. The combining/dividing means 5 is constituted by a WDM (Wavelength Division Multiplexing) coupler, for example, and functions to combine ad divide light beams according to a set cutoff wavelength. With regard to WDM couplers, it can be said that complete separation is achieved if isolation of −10 db or less is present. The combining/dividing means 5 combines the measuring light beams L1a and L1b that propagate thereto from the light dividing means 3a and 3b, and emits the combined light beam toward the probe 30. The combining/dividing means 5 divides the reflected light beams L3a and L3b that propagate thereto from the probe 30, ad emits the divided light beams toward the combining means 4a and 4b, respectively.

It is desirable for the cutoff wavelength of the combining/dividing means 5 to be set to a wavelength band between the wavelength band $\Delta\lambda a$ of the light beam La and the wavelength band $\Delta\lambda b$ of the light beam Lb. That is, it is desirable for the cutoff wavelength to be set within a wavelength band A illustrated in FIG. 2B. In this case, the reflected light beams L3a and L3b can be positively separated, and therefore the cutoff wavelength of the combining/dividing means 5 is set to this value in the present embodiment. Note that deterioration in light utilization efficiency can be minimized even if the number of light beams to be combined increases, by employing the WDM coupler as the combining/dividing means.

The reflected light beam L3a is combined with the reference light beam L2a by the combining means 4a, and the reflected light beam L3b is combined with the reference light beam L2b by the combining means 4b. Note that a transmissive type optical path length adjusting means 20a is provided in the optical path of the reference light beam L2a between the light dividing means 3a and the combining means 4a, and a transmissive type optical path length adjusting means 20b is provided in the optical path of the reference light beam L2b between the light dividing means 3b and the combining means 4b. The optical path length adjusting means 20a and 20b respectively change the optical path lengths of the reference light beams L2a and L2b, to adjust the position at where obtainment of a tomographic image is initiated.

The combining means 4 is constituted by a 2×2 optical fiber coupler having a division ratio of 50:50, for example. The combining means 4a combines the reflected light beam L3a with the reference light beam L2a, and emits the interference light beam 4a formed thereby toward the interference light detecting means 40a. Similarly, the combining means 4b combines the reflected light beam L3b with the reference light beam L2b, and emits the interference light beam 4b formed thereby toward the interference light detecting means 40b. The interference light detecting means 40a and 40b are configured to perform balanced detection of the divided interference light beams L4a and L4b using two photodetecting elements each. Therefore, the influence of fluctuations in optical intensity can be suppressed, and clearer images are enabled to be obtained.

The interference light detecting means 40a and 40b functions to respectively photoelectrically convert the interference light beams L4a and L4b, and to detect interference signals ISa and ISb, corresponding to the wavelength bands $\Delta\lambda a$ and $\Delta\lambda b$ of the light beams La and Lb. Here, the corresponding light beams can be discriminated, by synchronizing detection with the trigger of wavelength sweeping at the light sources 10a and 10b. At this time, the interference light detecting means 40a and 40b observes the interference signals ISa and ISb corresponding to each spectral component of light emitted by the light sources 10a and 10b. The interference signals ISa and ISb are output to the tomographic image processing means 50.

The tomographic image processing means 50 is realized by a computer system, such as a personal computer. The tomographic image processing means 50 administers frequency analysis on the interference signals ISa and ISb, which have been photoelectrically converted by the interference light detecting means 40a and 40b, to detect a plurality of pieces of intermediate tomographic data (reflectance) ra(z) and rb(z) regarding each depth position within the measurement target S. The tomographic image processing means 50 functions to obtain a tomographic image of the measurement target S, by employing the plurality of pieces of intermediate tomographic data ra(z) and rb(z). Specifically, the tomographic image processing means 50 comprises: a frequency analyzing means 51, for detecting the pieces of intermediate tomographic data ra(z) and rb(z) at each depth position within the measurement target S, by administering frequency analysis on each of the interference signals ISa and ISb; a tomographic data processing means 52, for generating tomographic data r(z), to be employed in generating the tomographic image, from the pieces of intermediate tomographic data ra(z) and rb(z) detected by the frequency analyzing means 51; and a tomographic image generating means 53, for generating the tomographic image, employing the tomographic data r(z) generated by the tomographic data processing means 52.

The frequency analyzing means 51 comprises: a first frequency analyzing means 51a for detecting intermediate tomographic data ra(z) based on the first light beam La, by administering frequency analysis on the first interference signals ISa; and a second frequency analyzing means 51b for detecting intermediate tomographic data rb(z) based on the second light beam Lb, by administering frequency analysis on the second interference signals ISb. Here, the method by which the first frequency analyzing means 51 calculates the intermediate tomographic data ra(z) based on the first interference signals ISa will be described briefly. Note that a detailed description of this method can be found in M. Takeda, "Optical Frequency Scanning Interference Microscopes", Optics Engineering Contact, Vol. 41, No. 7, pp. 426-432, 2003.

When the measuring light beam L1a is irradiated onto the measurement target S, the light intensity of the interference pattern generated by the reflected light beam L3a and the reference light beam L2a interfering with each other at various optical path length differences (depth positions within the measurement target), is designated as S(l). The light intensity I(k) detected by the interference light detecting means 40*a* is expressed by the following formula:

$$I(k) = \int_0^\infty S(l)[1+\cos(kl)]dl \quad (1)$$

Figure 4:
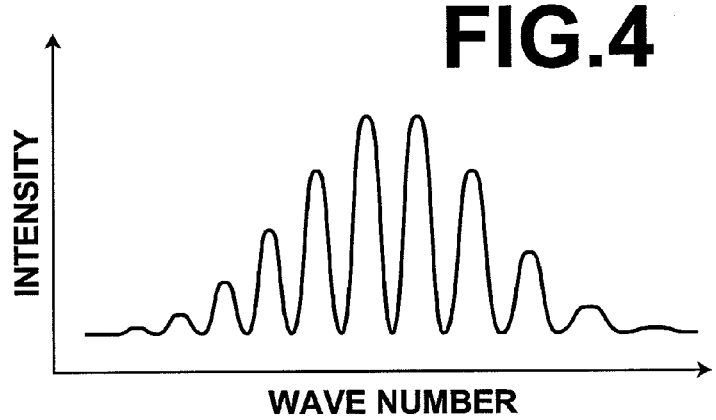
FIG. 4 is a graph that illustrates an example of an interference light beam detected by an interference light detecting means of FIG. 1.
Figure 5:
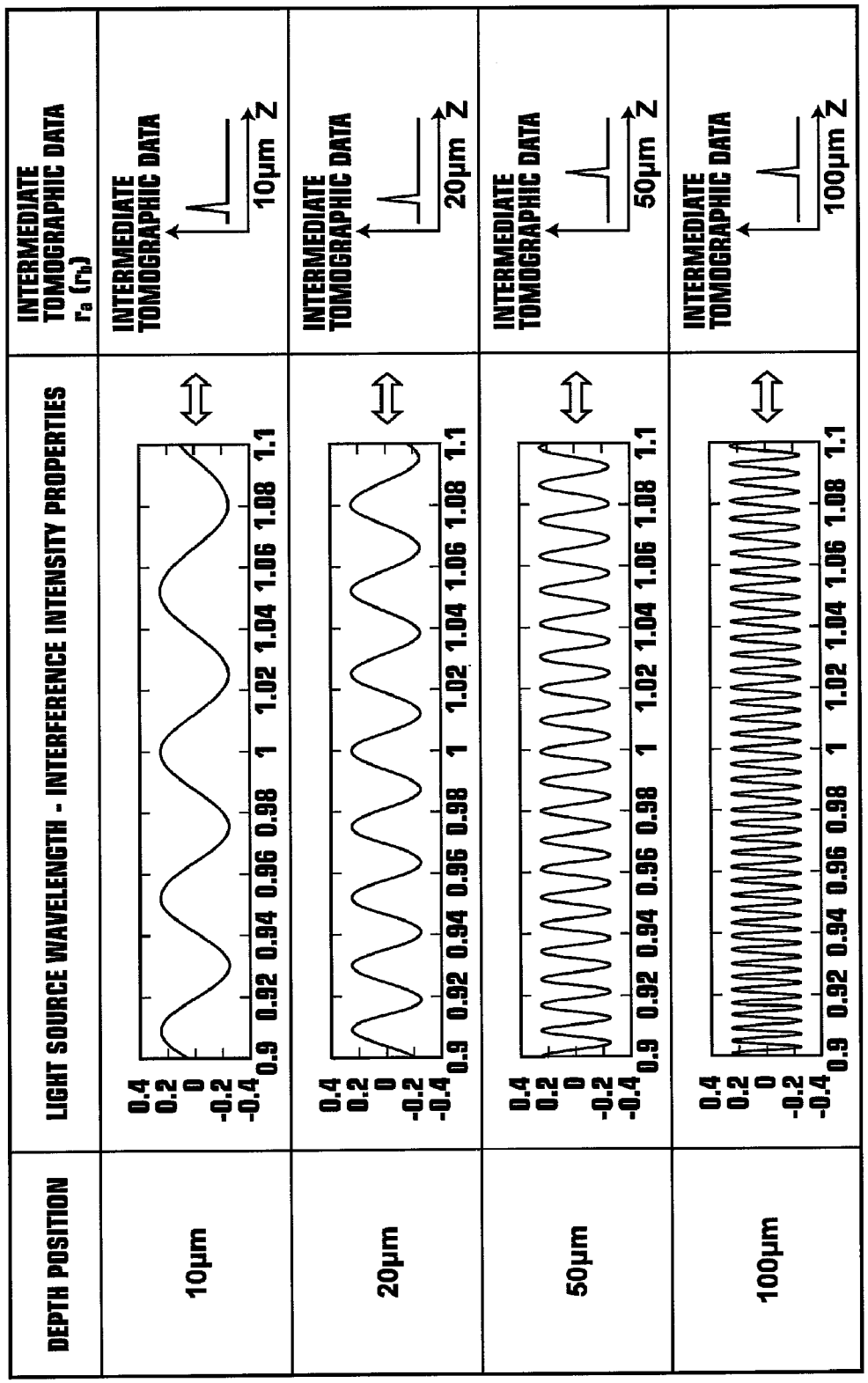
FIG. 5 is a table that illustrates tomographic data regarding each depth position within a measurement target, obtained by administering frequency analysis on the interference light beam detected by the interference light detecting means of FIG. 1.

Here, k represents the angular frequency, and l represents the optical path length difference between the reflected light beam L3*a* and the reference light beam L2*a*. An example of the light intensity I(k) detected by the interference light detecting means 40*a* is illustrated in the graph of FIG. 4. Formula (1) above may be considered as being provided as an interferogram of an optical frequency range, in which the wave number k is a variable. Accordingly, the first frequency analyzing means 51*a* performs frequency analysis by administering Fourier transform on the spectral interference pattern detected by the interference light detecting means 40*a*, to determine the optical intensity S(l) of the interference signals ISa for each wavelength, and to obtain the reflectance at each depth position within the measurement target S, as illustrated in FIG. 5. Then, the first frequency analyzing means 51*a* obtains data regarding the distances from a reference position within the measurement target S, and the intermediate tomographic data ra(z). Similarly, the second frequency analyzing means 51*b* obtains data regarding the distances from a measurement initiating position and the intermediate tomographic data rb(z), corresponding to the interference signals ISb. That is, the frequency analyzing means 51*a* and 51*b* obtains the plurality of pieces of intermediate tomographic data ra(z) and rb(z) from the same portion of the measurement target S, onto which the measuring light beams L1*a* and L1*b* are irradiated. Note that the method by which the frequency analyzing means 51 obtains the intermediate tomographic data ra(z) and rb(z) is not limited to the aforementioned Fourier transform process. Alternatively, other known spectral analyzing techniques, such as the Maximum Entropy Method and the Yule-Walker method may be employed.

Figure 3:
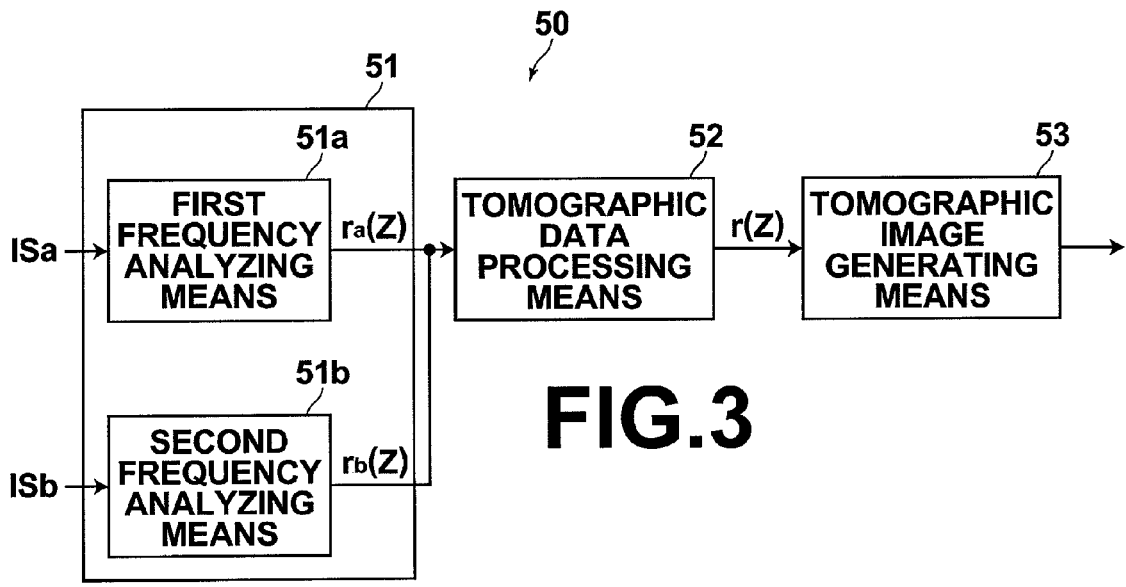
FIG. 3 is a block diagram that illustrates a example of the construction of a tomographic image processing means of FIG. 1.

The tomographic data processing means 52 illustrated in FIG. 3 detects the tomographic data r(z), which is employed to generate the tomographic image, from the plurality of pieces of intermediate tomographic data ra(z) and rb(z) detected for each depth position within the measurement target S. Specifically, the tomographic data processing means 52 calculates the tomographic data r(z) as average values of the intermediate tomographic data ra(z) and rb(z), according to the formula: r(z)={ra(z)+ra(b)}/2.

The tomographic image generating means 53 generates the tomographic image, employing the tomographic data r(z) detected by the tomographic data processing means 52. Specifically, the measuring light beams L1*a* and L1*b* are irradiated onto the measurement target S, while being scanned in a direction perpendicular to the depth direction z thereof. Thereby, the tomographic image generating means 53 tomographic data r(z) regarding each depth position of the measurement target S at a plurality of measurement points. Thereafter, the tomographic image generating means 53 generates a two dimensional or three dimensional tomographic image, employing the obtained tomographic data r(z).

The tomographic data processing means 52 of the tomographic image processing means 50 obtains the tomographic data r(z) by calculating the average values of the plurality of pieces of intermediate tomographic data ra(z) and rb(z), as described above. Therefore, noise components and the like, which are included in each of the intermediate tomographic data ra(z) and rb(z), can be cancelled out, to improve the image quality of the generated tomographic image.

The absolute value of the tomographic data regarding each depth position z within the measurement target S differs for each wavelength of the irradiated measurement light beams L1*a* and L1*b*. These differences are caused by various factors, such as light absorption properties and light scattering properties based on the composition of the measurement target S. However, the measuring light beams L1*a* and L1*b* are simultaneously irradiated on the same portion of the measurement target S. Therefore, even if the values of the intermediate tomographic data ra(z1) and rb(z1) obtained at a given depth position z1 are different, the qualitative properties thereof, such as the peak positions at where the tomographic data are maximal, are substantially the same.

The noise components included in the intermediate tomographic data ra(z1) and rb(z1) can be cancelled out, by calculating an average value r(z1) thereof, to emphasize the component that represents the tomographic data at the depth position z1, even if the values of the intermediate tomographic data are different. Accordingly, a tomographic image having high image quality can be obtained, even in the case that the tomographic image is obtained by employing the discrete light beams La and Lb instead of a light beam emitted by a wide band light source.

Note that the sampling pitch with respect to the Fourier transform performed by the frequency analyzing means 51 depends on the widths of the wavelength bands Δλa and Δλb of the light beams La and Lb. For this reason, if the widths of the wavelength bands λ1 and λ2 are different as described above, the sampling pitches for the interference signals ISa and ISb are also different. In this case, the widths of the wavelength bands Δλa and Δλb can be uniformized, by inserting 0 values to the interference signals ISa, which are obtained from the light beam La having the narrower wavelength band.

In addition, a case has been described in which the average values of the intermediate tomographic data ra(z) and rb(z) are calculated. Alternatively, the products of the intermediate tomographic data ra(z) and rb(z) may be employed as the tomographic data r(z). In this case, the highest signal components within the intermediate tomographic data ra(z) and rb(z) are reinforced by multiplication. Therefore, the signal values of noise components are relatively decreased, and tomographic images having high image quality can be obtained. Further, methods other than those described above may be employed to generate the tomographic data r(z) regarding each depth position of the measurement target S, employing the intermediate tomographic data ra(z) and rb(z). Thereafter, tomographic images constituted by pixel signals based on the tomographic data r(z) may be generated.

In the embodiment described above, a case in which the average values of the intermediate tomographic data ra(z) and rb(z) are employed to obtain the tomographic data r(z) has been described as an example. Alternatively, data regarding the spectra of the light beams La and Lb emitted by the light source unit 10 may be employed to combine the intermediate tomographic data ra(z) and rb(z) while taking the wavelength bands of the interference signals ISa and ISb. This enables obtainment of the tomographic data (reflectance intensities) r(z) at high resolution. That is, the intermediate tomographic data ra(z) and rb(z), which are obtained by administering Fourier transform on the interference signals ISa and ISb, have the following relationships with the true reflectance intensities r(z) and ha(z) and hb(z), which are the spectral shapes of the light beams La and Lb on which Fourier transform has been administered:

$$ra(z) = r(z) \otimes ha(z) \quad (2)$$

$$rb(z) = r(z) \otimes hb(z) \quad (3)$$

wherein ⊗ represents a convolution operation.

If these relationships are discretely expressed as $ra=[ra(0), ra(1\times dz_a), \ldots]^T$, $rb=[rb(0), rb(1\times dz_b), \ldots]^T$, and $r=[r(0), r(1\times dz), \ldots]$ the relationships can be expressed by the following formulas:

$$Ha \cdot r = ra \quad (4)$$

$$Hb \cdot r = rb \quad (5)$$

Here, Ha and Hb are matrices constituted by each vector of ha=[ha(0), ha(1×dz), . . . ] and hb=[hb(0), hb(1×dz), . . . ], of which the elements are shifted while being arranged. The reflectance intensities r can be obtained as optimized solutions to these relational expressions, by known techniques such as the recursion method.

The reflectance intensities r(z) can be calculated more accurately from relational expressions that take the differences in wavelength bands of the light beams La and Lb into consideration. Therefore, higher resolution tomographic images can be generated.

Next, the operation of the optical tomograph 1 will be described with reference to FIGS. 1 through 6. First, the light source 10a emits the light beam La, of which the wavelength is swept within the wavelength band Δλa at a predetermined period. The light beam La is guided by the optical fiber FB1a, and enters the light dividing means 3a. The light dividing means 3a divides the light beam La into the measuring light beam L1a and the reference light beam L2a. The measuring light beam L1a is emitted toward an optical fiber FB2a, and the reference light beam L2a is emitted toward an optical fiber FB3a. The measuring light beam L1a propagates through the optical fiber FB2a, and enters the combining/dividing means 5 via a circulator 15a and an optical fiber FB4a.

Meanwhile, the light source 10b emits the light beam Lb, of which the wavelength is swept within the wavelength band Δλb at a predetermined period. The light beam Lb is guided by the optical fiber FB1b, and enters the light dividing means 3b. The light dividing means 3b divides the light beam Lb into the measuring light beam L1b and the reference light beam L2b. The measuring light beam L1b is emitted toward an optical fiber FB2b, and the reference light beam L2b is emitted toward an optical fiber FB3b. The measuring light beam L1b propagates through the optical fiber FB2b, and enters the combining/dividing means 5 via a circulator 15b and an optical fiber FB4b.

The combining/dividing means 5 combines the measuring light beams L1a and L1b. The combined light beam propagates through the optical fiber FB5, enters the probe 30 via the optical rotary connector 31, propagates through the probe 30, and is irradiated onto the measurement target S. The reflected light beams L3a and L3b, which are reflected at each depth position z within the measurement target S, reenters the probe 30. The reflected light beams L3a and L3b enter the combining/dividing means 5 via a route reverse to that through which the measuring light beams L1a and L1b propagated.

The cutoff wavelength of the combining/dividing means 5 is set within the wavelength band Δ illustrated in FIG. 2B, as described above. Therefore, the combining/dividing means 5 divides the reflected light beam L3a and the reflected light beam L3b. The reflected light beam L3a is emitted toward the optical fiber FB4a, and the reflected light beam L3b is emitted toward the optical fiber FB4b.

The reflected light beam L3a, which is guided through the optical fiber FB4a, enters the combining means 4a via the circulator 15a and an optical fiber FB6a. Meanwhile, the reference light beam L2a enters the combining means 4a after the optical path length thereof is changed by the optical path length adjusting means 20a provided along the optical fiber FB3a.

The combining means 4a combines the reflected light beam L3a and the reference light beam L2a, and the interference light beam L4a formed thereby is split into two light beams and emitted toward the interference light detecting means 40a. The interference light detecting means 40a performs balanced detection and photoelectric conversion of the interference light beam L4a, to generate interference signals ISa, which are output to the tomographic image processing means 50.

Similarly, the reflected light beam L3b, which is guided through the optical fiber FB4b, enters the combining means 4b via the circulator 15b and an optical fiber FB6b. Meanwhile, the reference light beam L2b enters the combining means 4b after the optical path length thereof is changed by the optical path length adjusting means 20b provided along the optical fiber FB3b.

The combining means 4b combines the reflected light beam L3b and the reference light beam L2b, and the interference light beam L4b formed thereby is split into two light beams and emitted toward the interference light detecting means 40b. The interference light detecting means 40b performs balanced detection and photoelectric conversion of the interference light beam L4b, to generate interference signals ISb, which are output to the tomographic image processing means 50.

The tomographic image processing means 50 detects the plurality of pieces of intermediate tomographic data ra(z) and rb(z) regarding each depth position of the measurement target S from the interference signals ISa and ISb. Then, the tomographic data r (z), which is employed to generate the tomographic image, are calculated from each piece of the intermediate tomographic data ra(z) and rb(z). Thereafter, the two dimensional optical tomographic image is generated. The generated tomographic image is displayed by a display device 60 constituted by a CRT (Cathode Ray Tube) or a liquid crystal display, which is connected to the tomographic image processing means 50.

As described above, the optical tomograph 1 irradiates the light beams La and Lb, of which the wavelengths are swept within different wavelength bands, onto the measurement target S. The interference light beams L4a and L4b generated thereby are detected by different interference light detecting means 40a and 40b, corresponding to each wavelength band. Thereby, high resolution images can be obtained at high speed.

Note that in the description of the optical tomograph 1 according to the first embodiment, a case was described in which the light beams La and Lb had discrete wavelength bands. However, the present invention is not limited to this configuration, and the light beams La and Lb may have overlapping wavelength bands, as will be described as a second embodiment of the present invention below.

Figure 7:
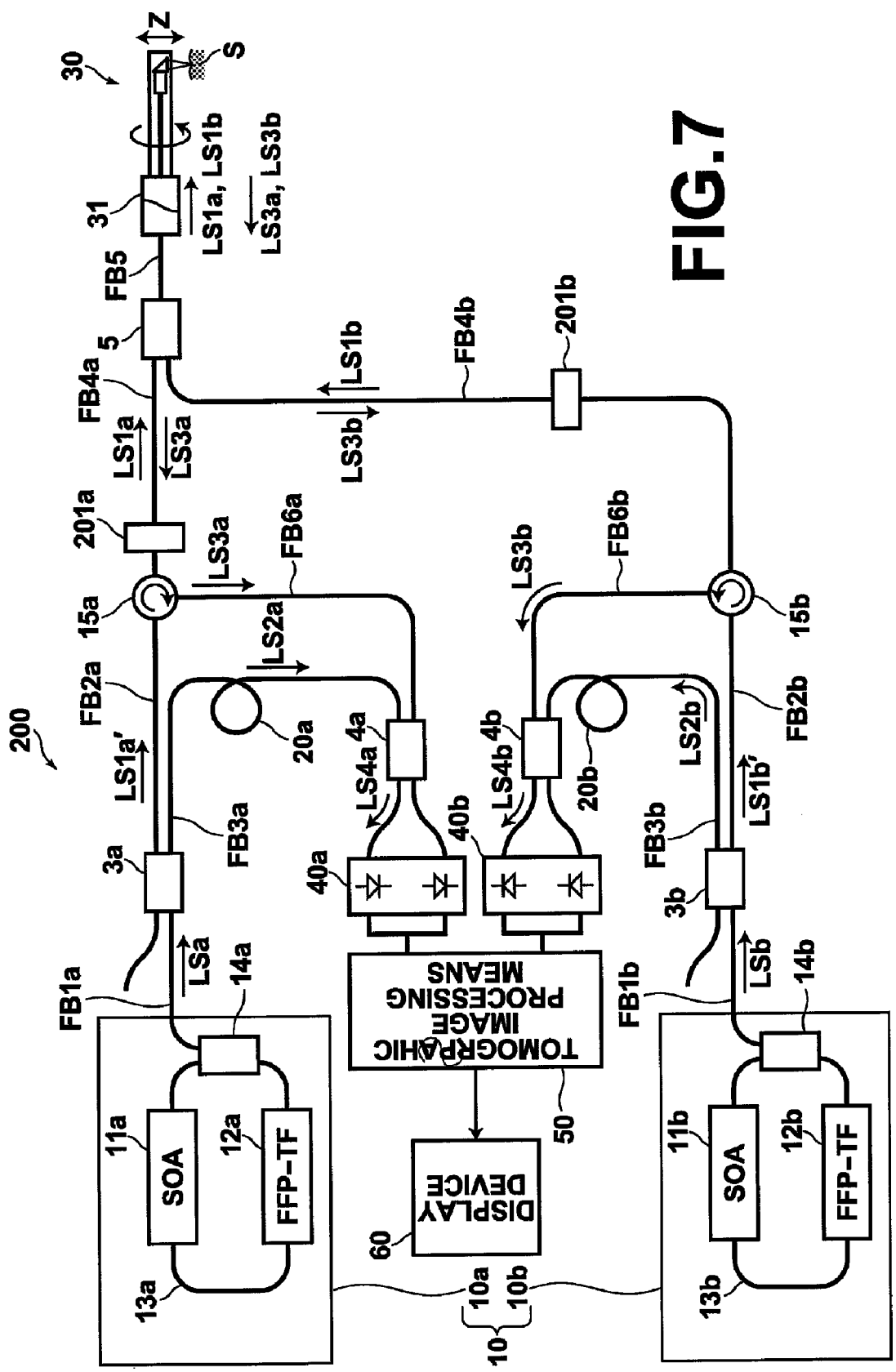
FIG. 7 is a diagram that illustrates the schematic construction of an optical tomograph according to a second embodiment of the present invention.

Hereinafter, an optical tomograph 200 according to the second embodiment of the present invention will be described with reference to FIG. 7, FIG. 8A, and FIG. 8B. FIG. 7 is a diagram that illustrates the schematic construction of the optical tomograph 200. Note that in FIG. 7, components of the optical tomograph 200 which are the same as those of the optical tomograph 100 of FIG. 1 are denoted with the same reference numerals, and that detailed descriptions thereof will be omitted, insofar as they are not particularly necessary. The optical tomograph 200 of FIG. 7 differs from the optical tomograph 100 of FIG. 1 in the wavelength bands of the light beams LSa and LSb emitted by the light source 10, and in that optical filters 201a and 201b are provided. Hereinafter, a description will be given mainly regarding the differences between the optical tomograph 200 and the optical tomograph 100.

Figure 8A:
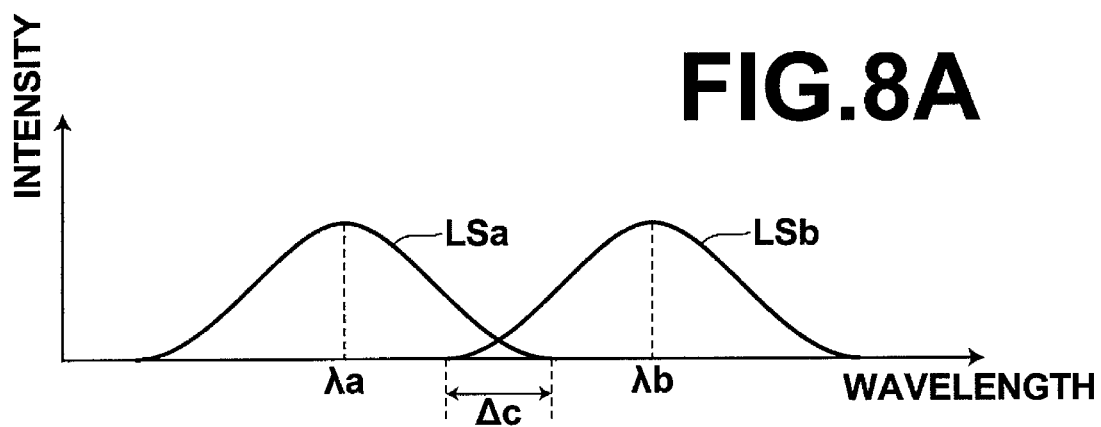
FIG. 8A is a graph that illustrates the spectra of light beams emitted by a light source unit of FIG. 7.

The wavelengths of the light beams LSa and LSb emitted by the light source unit 10 of the optical tomograph 200 are swept within different wavelength bands at the same period, but a portion of the wavelength bands overlap, as indicated by the wavelength band Δc indicated in FIG. 8A. If OCT measurement is performed by an optical tomograph having the same construction as that of the optical tomograph 100 using these light beams LSa and LSb, it will not be possible to divide the light beams at the combining/dividing means 5. That is, interference signals corresponding to two light beams will be inseparably mixed in each of the interference detecting means.

Therefore, the optical tomograph 200 comprises optical filters 201a and 201b, which are provided along the optical path of the measuring light beams between the light sources 10a, 10b and the combining/dividing means 5.

In the optical tomograph 200 of FIG. 7, the light beam LSa is divided into a measuring light beam LS1a' and a reference light beam LS2a by the light dividing means 3a. The measuring light beam LS1a' is guided through the optical fiber FB2a, and is emitted toward the optical fiber FB4a via the circulator 15a. The measuring light beam LS1a' enters the optical filter 201a, which is provided along the optical fiber FB4a. The optical filter 201a filters out light within the wavelength range Δc from the measuring light beam LS1a', to obtain a measuring light beam LS1a having a spectrum as illustrated in FIG. 8B.

Figure 8B:
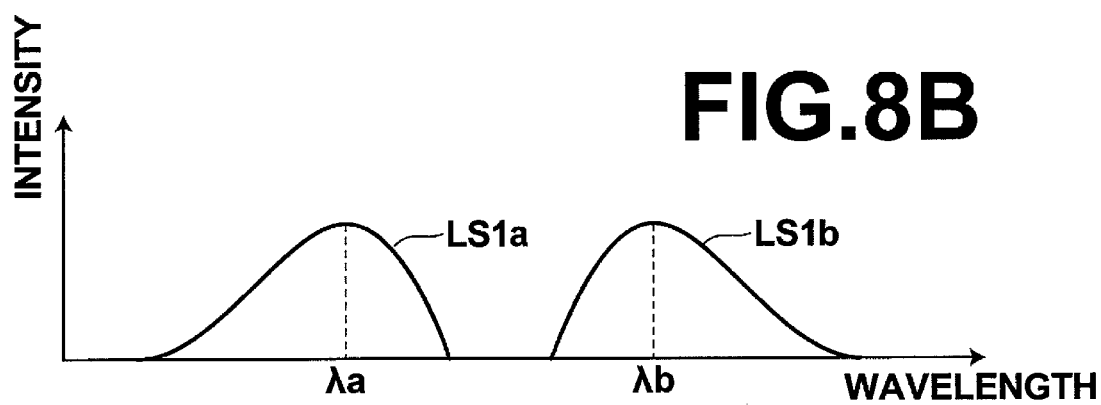
FIG. 8B is a graph that illustrates the spectra of the light beams of FIG. 7 after an optical filter is applied.

A reflected light beam LS3a, which is the measuring light beam LS1a reflected by the measurement target S has the same spectrum as that of the measuring light beam LS1a illustrated in FIG. 8B. The reflected light beam LS3a also passes through the optical filter 201a as it propagates through the optical fiber FB4a. However, no change in spectrum occurs, because the reflected light beam LS3a does not include any light components within the wavelength band Δc. The combining means 4a combines the reflected light beam LS3a with the reference light beam LS2a. The interference light beam LS4a generated thereby also has the same spectrum as that of the measuring light beam LS1a illustrated in FIG. 8B.

Similarly, the light beam LSb is divided into a measuring light beam LS1b' and a reference light beam LS2b by the light dividing means 3b. The measuring light beam LS1b' is guided through the optical fiber FB2b, and is emitted toward the optical fiber FB4b via the circulator 15b. The measuring light beam LS1b' enters the optical filter 201b, which is provided along the optical fiber FB4b. The optical filter 201b filters out light within the wavelength range Δc from the measuring light beam LS1b', to obtain a measuring light beam LS1b having a spectrum as illustrated in FIG. 8B.

A reflected light beam LS3b, which is the measuring light beam LS1b reflected by the measurement target S has the same spectrum as that of the measuring light beam LS1b illustrated in FIG. 8B. The reflected light beam LS3b also passes through the optical filter 201b as it propagates through the optical fiber FB4b. However, no change in spectrum occurs, because the reflected light beam LS3b does not include any light components within the wavelength band Δc. The combining means 4b combines the reflected light beam LS3b with the reference light beam LS2b. The interference light beam LS4b generated thereby also has the same spectrum as that of the measuring light beam LS1b illustrated in FIG. 8B.

The other operations of the optical tomograph 200 are the same as those of the optical tomograph 1.

By providing the optical filters 201a and 201b, OCT measurement equivalent to that performed by the light beams LS1a And LS1b having discrete wavelength bands illustrated in FIG. 8B can be performed, even if the wavelength bands of the light beams emitted by the light source unit 10 overlap. Accordingly, the interference light beams L4a and L4b can be separated corresponding to the light beams LSa and LSb, and detected by different interference light detecting means 40a and 40b. Therefore, inseparable mixing of the interference signals corresponding to different light beams can be prevented.

Note that the possibility of mixing occurring among interference signals depends on the relationship between the wavelength band of each light beam and the cutoff wavelength of the combining/dividing means 5. For example, in the case that a portion of the wavelength band of the light beam La emitted by the optical tomograph 1 is in the vicinity of the cutoff wavelength of the combining/dividing means 5, a portion of the interference light beam L4a enters the interference light detecting means 40b, and becomes noise with respect to the interference signals output thereby. In this case as well, mixing of the interference signals can be prevented, by providing the light shielding optical filters as described above.

Note that in the example illustrated in FIG. 7, the optical filters 201a and 201b are provided upstream of the combining/dividing means 5. However, the optical filters 201a and 201b may be provided anywhere along the optical path between the light source unit 10 and the interference light detecting means 40a and 40b.

In addition, in the example illustrated in FIG. 7, two optical filters are provided. Depending on the cutoff frequency of the combining/dividing means 5, however, only a single optical filter may be provided, as long as each interference light detecting means detects an interference light beam based on a single light beam.

In the second embodiment described above, the optical filters were provided to optically remove the overlapping wavelength band Δc. Alternatively, in the case that the wavelength band Δc is known in advance, the tomographic image processing means 50 may perform signal processing to remove the overlapping wavelength band Δc, as will be described as a third embodiment of the present invention.

Figure 9:
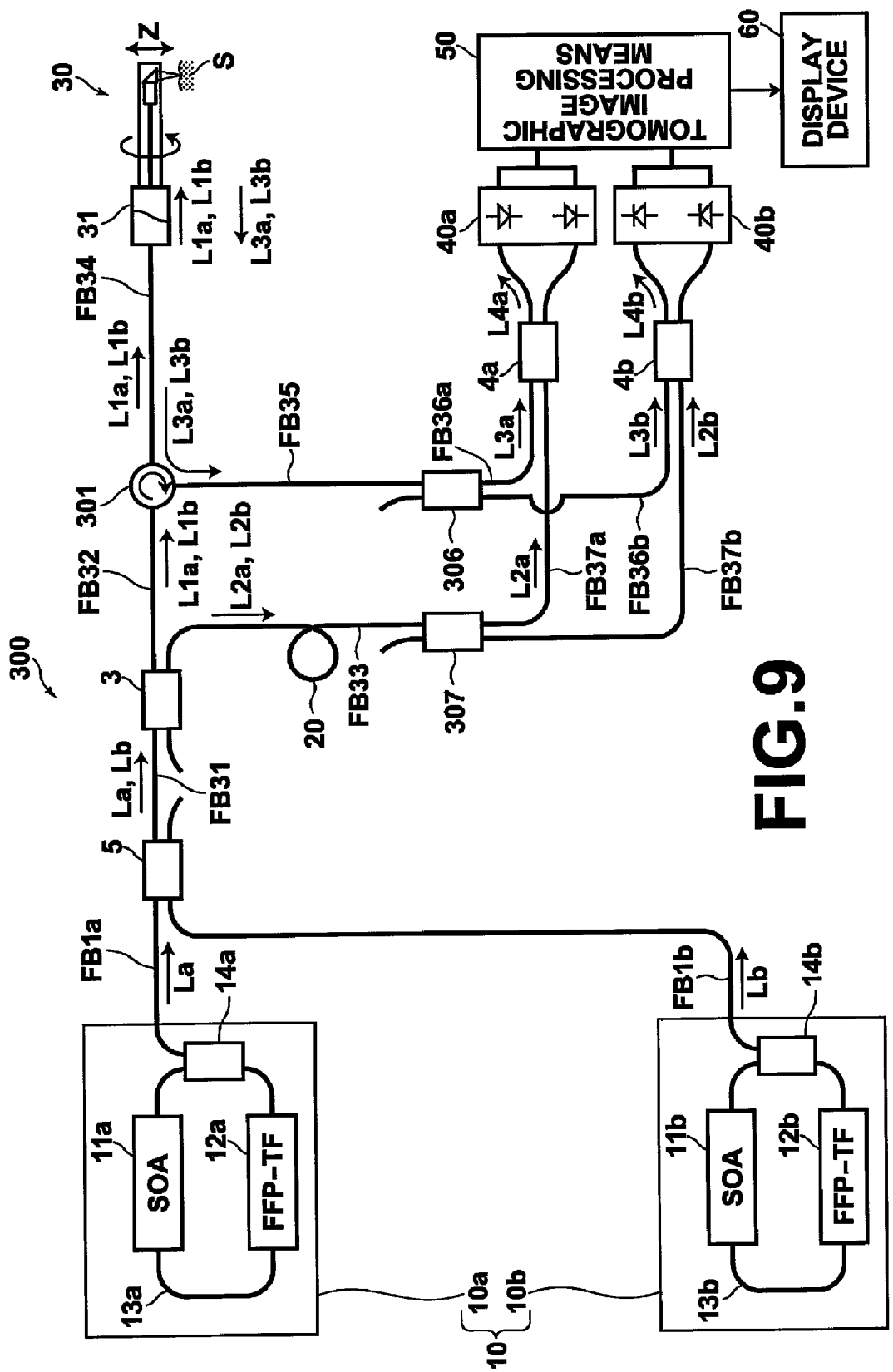
FIG. 9 is a diagram that illustrates the schematic construction of an optical tomograph according to a third embodiment of the present invention.

Next, an optical tomograph 300 according to the third embodiment of the present invention will be described with reference to FIG. 9. FIG. 9 is a diagram that illustrates the schematic construction of the optical tomograph 300. Note that in FIG. 9, components of the optical tomograph 300 which are the same as those of the optical tomograph 100 of FIG. 1 are denoted with the same reference numerals, and that detailed descriptions thereof will be omitted, insofar as they are not particularly necessary. The optical tomograph 300 is an SS-OCT apparatus that employs a Mach-Zehnder interferometer. The optical tomograph 300 differs from the optical tomograph 100 in that the combining/dividing means 5 is provided upstream of the interferometer. Hereinafter, a description will be given mainly regarding the differences between the optical tomograph 300 and the optical tomograph 100.

In the optical tomograph 300, the light beam La emitted by the light source 10a propagates through the optical fiber FB1a, and enters the combining/dividing means 5. The light beam Lb emitted by the light source 10b propagates through the optical fiber FB1b, and enters the combining/dividing means 5. The combining/dividing means 5 combines the light beams La and Lb, and the combined light beam enters the light dividing means 3 via an optical fiber FB31.

The light dividing means 3 is constituted by a 2×2 optical fiber coupler with a division ratio of 90:10, for example. The light dividing means 3 functions to divide the light beams La and Lb into the measuring light beams L1a, L1b and the reference light beams L2a, L2b. The measuring light beams L1a and L1b are guided through an optical fiber FB32, and are irradiated onto the measurement target S via a circulator 301, an optical fiber FB34, and the probe 30. The reflected light beams L3a and L3b reflected by the measurement target S enter a reflected light separating means 306 via the probe 30, the optical fiber FB34, the circulator 301, and an optical fiber FB35.

The reflected light separating means 306 has wavelength selectivity, and is constituted by a WDM coupler, for example. The reflected light separating means 306 emits the reflected light beam L3a of the same wavelength band as the light beam La toward an optical fiber FB36a, and emits the reflected light beam L3b of the same wavelength band as the light beam Lb toward an optical fiber FB36b. The combining means 4a is linked to the optical fiber FB36a, and the combining means 4b is linked to the optical fiber FB36b.

Meanwhile, the reference light beams L2a and L2b are guided through an optical fiber FB33, and enter a reference light separating means 307 after the optical path lengths thereof are changed by the optical path length adjusting means 20 provided along the optical fiber FB33.

The reference light separating means 307 has wavelength selectivity, and is constituted by a WDM coupler, for example. The reflected light separating means 307 emits the reference light beam L2a of the same wavelength band as the light beam La toward an optical fiber FB37a, and emits the reference light beam L2b of the same wavelength band as the light beam Lb toward an optical fiber FB37b. The combining means 4a is linked to the optical fiber FB37a, and the combining means 4b is linked to the optical fiber FB37b.

The combining means 4a combines the reflected light beam L3a with the reference light beam L2a, and the interference light beam L4a formed thereby is split into two light beams and emitted toward the interference light detecting means 40a. The combining means 4b combines the reflected light beam L3b with the reference light beam L2b, and the interference light beam L4b formed thereby is split into two light beams and emitted toward the interference light detecting means 40b.

The structures and operations of the interference light detecting means 40a, 40b, and the tomographic image processing means 50 are the same as those of the first embodiment, and therefore further descriptions thereof will be omitted.

Figure 10A:
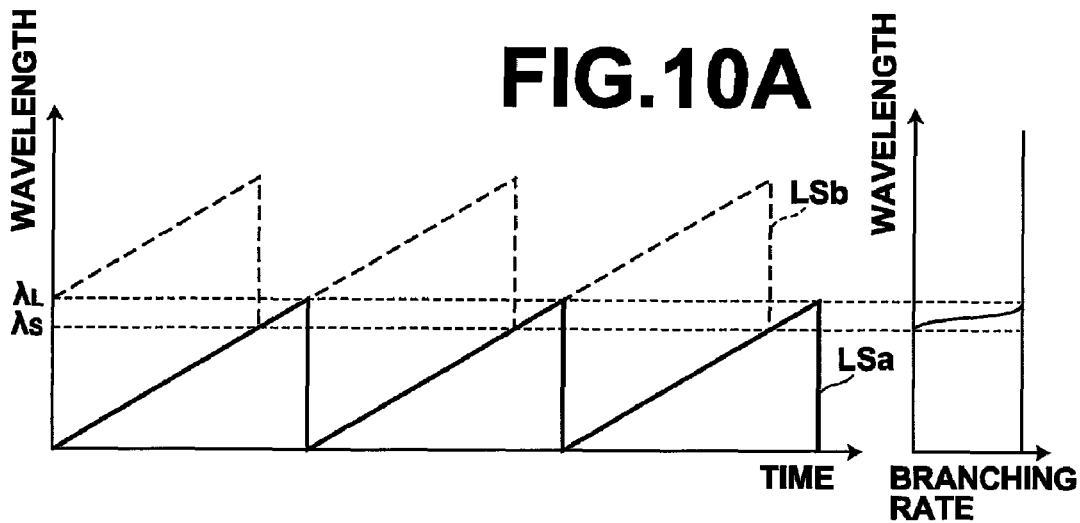
FIGS. 10A, 10B, 10C, and 10D are graphs for explaining the operation of a modification to the third embodiment of the present invention.

Hereinafter, a case in which the wavelength bands of the light beams LSa and LSb emitted by the light source unit 10 overlap as illustrated in FIG. 8A, and the interference signals based on light within the overlapping wavelength band Δc are removed by the tomographic image processing means 50 will be described as a modification to the third embodiment with reference to FIGS. 10A, 10B, 10C, and 10D. The graph at the left side of FIG. 10A illustrates the manner in which wavelength sweeping is performed for the two light beams LSa and LSb, of which the wavelength bands overlap. In the graph at the left side of FIG. 10A, the horizontal axis represents time, and the vertical axis represents wavelength. The graph at the right side of FIG. 10A illustrates the branching properties of the light beams, corresponding to the wavelength axis of the graph at the left side. In the graph at the right side of FIG. 10A, the vertical axis represents wavelength, and the horizontal axis represents the branching ratio at the reflected light separating means 306 and the reference light separating means 306. In this modification, the reflected light separating means 306 and the reference light separating means 307 are configured such that the branching ratio varies from approximately 0% to 100% within the wavelength band Δc. The shortest wavelength within the wavelength band Δc is designated as $\lambda_S$, and the longest wavelength within the wavelength band Δc is designated as $\lambda_L$. Interference signals based on light having wavelengths of $\lambda_S$ through $\lambda_L$ are those that will become mixed signals. Therefore, timings at which the two light sources 10a and 10b sweep the wavelengths of the light beams emitted thereby are set such that the interference signals based on light having wavelengths of $\lambda_S$ through $\lambda_L$ occur during the same time period, as illustrated in FIG. 10A.

Figure 10B:
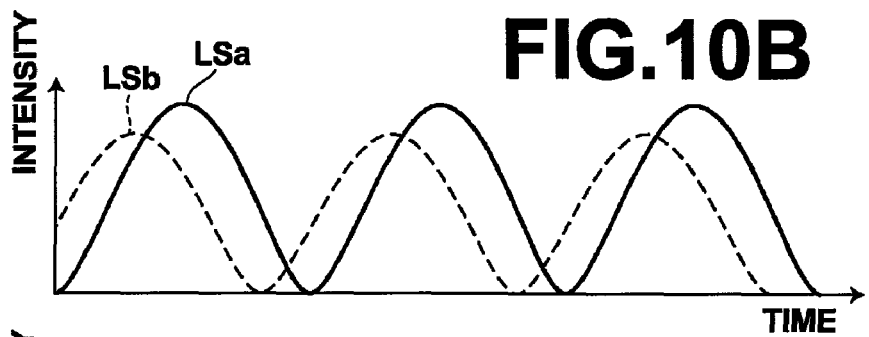
Figure 10C:
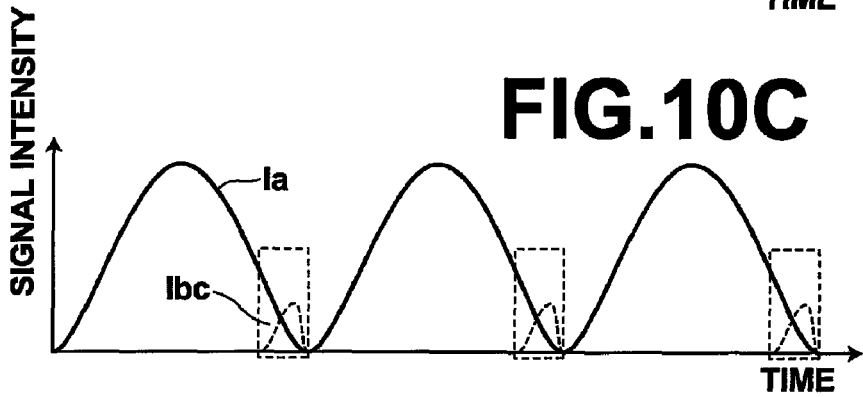
Figure 10D:
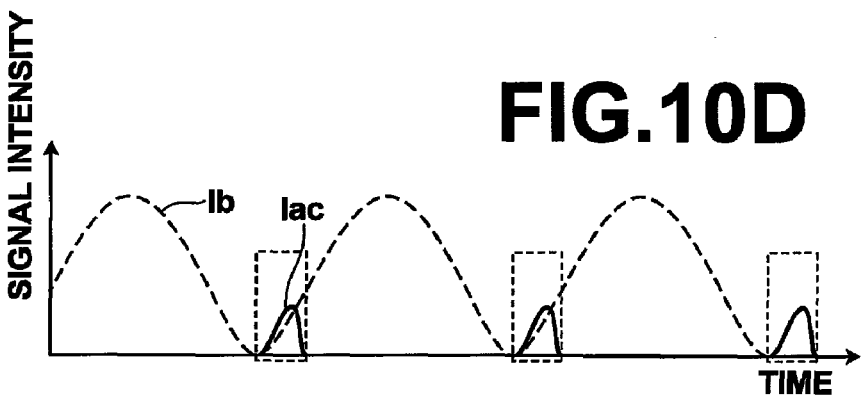

FIG. 10B is a graph that illustrates temporal changes in the intensities of the light beams LSa and LSb emitted by the light sources 10a and 10b. In the graph of FIG. 10B, the horizontal axis represents time, and the vertical axis represents intensity. FIG. 10C is a graph that illustrates changes in the intensities of interference signals output by the interference light detecting means 40a. FIG. 10D is a graph that illustrates changes in the intensities of interference signals output by the interference light detecting means 40b. The graphs of FIG. 10C and FIG. 10D correspond to the temporal axis of the graph of FIG. 10B. To facilitate understanding, the interference signals are separated into those corresponding to each of the light beams La and Lb.

Due to the properties of the combining/dividing means 5 illustrated in FIG. 10A, the wavelength band of light detected by the interference light detecting means 40a is $\lambda_L$ or less. Therefore, the interference signals output by the interference light detecting means 40a include signals Ia, which are based on the light beam LSa, and signals Ibc, which are based on light within the wavelength band $\lambda_S$ through $\lambda_L$ of the light beam LSb. Similarly, the wavelength band of light detected by the interference light detecting means 40b is $\lambda_S$ or greater. Therefore, the interference signals output by the interference light detecting means 40b include signals Ib, which are based on the light beam LSb, and signals Iac, which are based on light within the wavelength band $\lambda_S$ through $\lambda_L$ of the light beam LSa.

Therefore, the tomographic image processing means 50 performs processes to remove signals within the regions surrounded by the broken lines in FIG. 10C and FIG. 10D. That is, the tomographic image processing means 50 removes the signals based on light within the wavelength band $\lambda_S$ through $\lambda_L$. Thereby, OCT measurement equivalent to that performed by light beams LS1a and LS1b having discrete wavelength bands illustrated in FIG. 8B can be performed, even if the wavelength bands of the light beams emitted by the light source unit 10 overlap.

Figure 11:
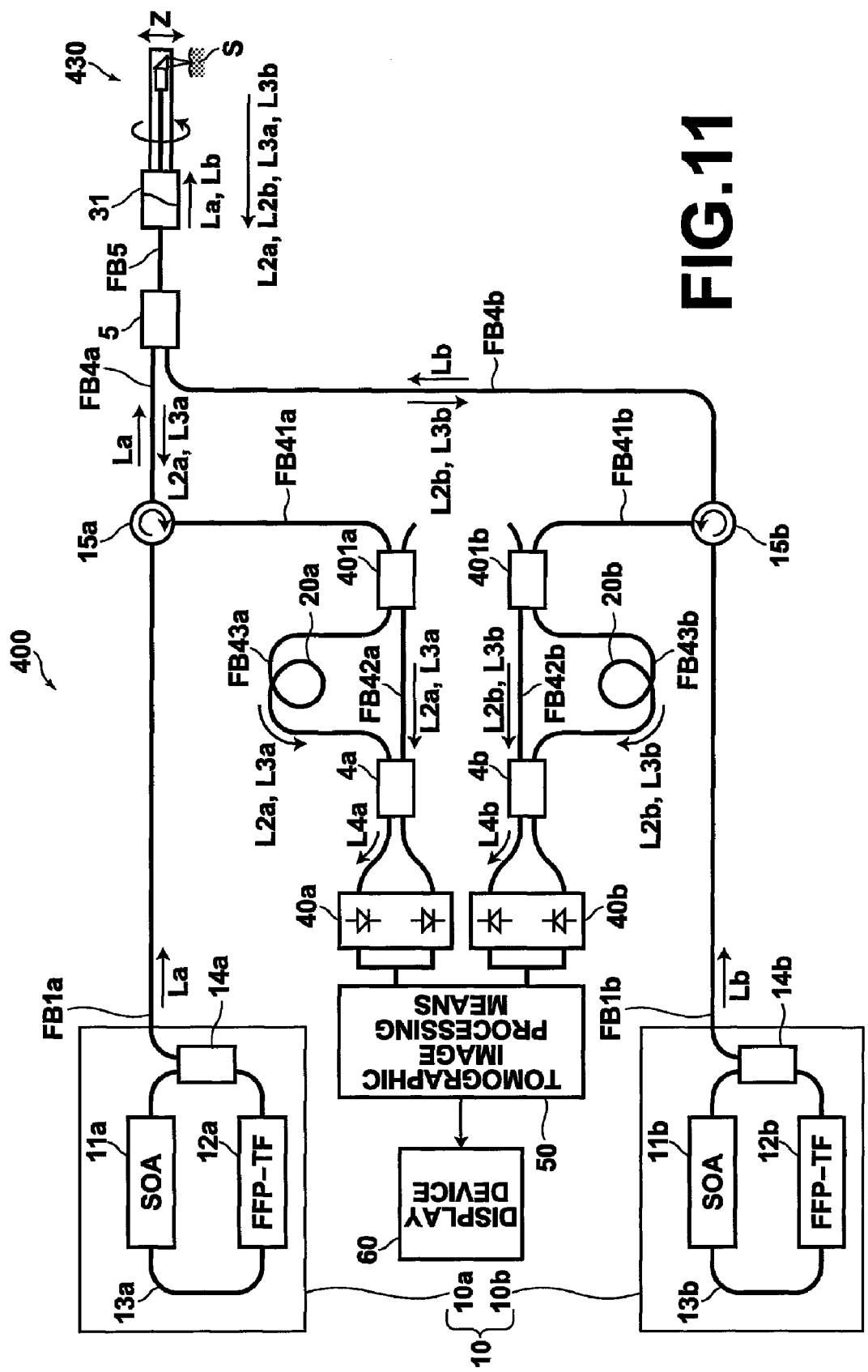
FIG. 11 is a diagram that illustrates the schematic construction of an optical tomograph according to a fourth embodiment of the present invention.
Figure 12:
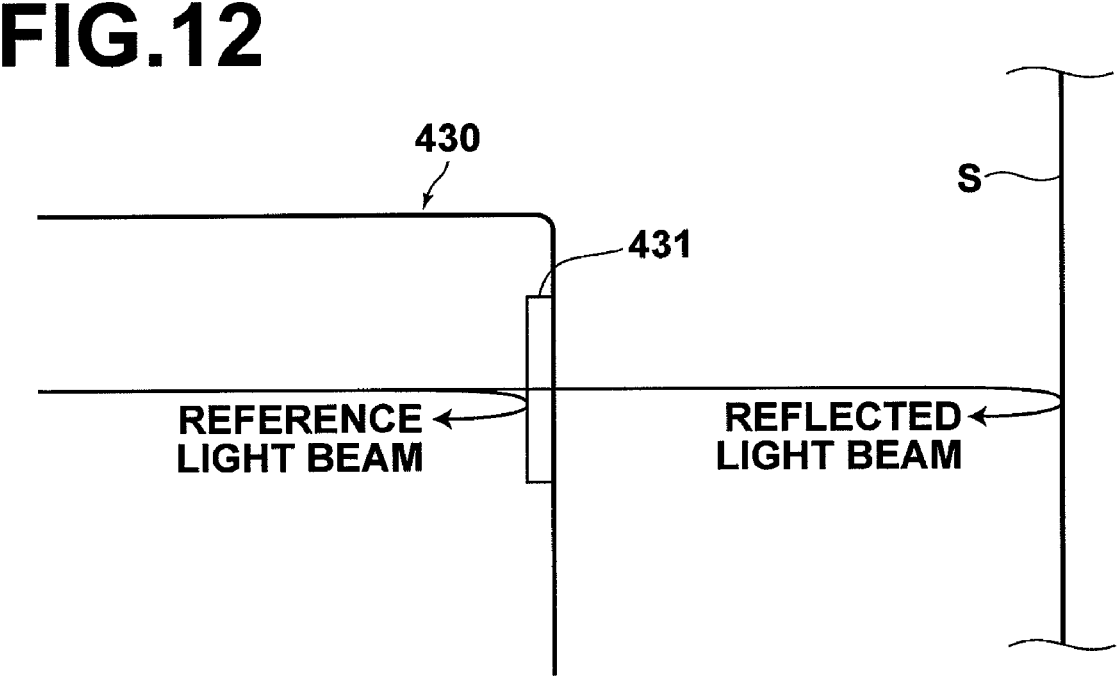
FIG. 12 is a diagram for explaining a Fizeau interferometer of FIG. 11.

Next, an optical tomograph 400 according to a fourth embodiment of the present invention will be described with reference to FIG. 11 and FIG. 12. FIG. 11 is a diagram that illustrates the schematic construction of the optical tomograph 400. Note that in FIG. 11, components of the optical tomograph 400 which are the same as those of the optical tomographs of the previous embodiments are denoted with the same reference numerals, and that detailed descriptions thereof will be omitted, insofar as they are not particularly necessary. The optical tomograph 400 is an SS-OCT apparatus that employs a Fizeau interferometer. The optical tomograph 400 differs from the optical tomograph 100 in that a probe 430 is employed instead of the probe 30. Hereinafter, a description will be given mainly regarding the differences between the optical tomograph 40 and the optical tomograph 100.

In the optical tomograph 400, the light beam La, which is emitted by the light source 10a, enters the combining/dividing means 5 via the optical fiber FB1a, the circulator 15a, and the optical fiber FB4a. Similarly, the light beam Lb, which is emitted by the light source 10b, enters the combining/dividing means 5 via the optical fiber FB1b, the circulator 15b, and the optical fiber FB4b.

The combining/dividing means 5 combines the light beam La and the light beam Lb, and the combined light beam enters the probe 430 via the optical fiber FB5 and the optical rotary connector 31. A light dividing means 431 provided at the light emitting end of the probe 430 transmits a portion of the light beams La, Lb as measuring light beams L1a, L1b, and the remaining portion is reflected as reference light beams L2a, L2b. The measuring light beams L1a, L1b are irradiated onto the measurement target S, and the reflected light beams L3a, L3b reflected thereby enter the combining/dividing means 5 via the probe 430 and the optical fiber FB5. The reference light beams L2a, L2b reflected by the light dividing means 431 also enter the combining/dividing means 5 via the probe 430 and the optical fiber FB5.

The reflected light beams L3a, L3b and the reference light beams L2a, L2b that enter the combining/dividing means 5 are divided according to the wavelength band thereof. The reflected light beam L3a and the reference light beam L2a are emitted toward the optical fiber FB4a, and the reflected light beam L3b and the reference light beam L2b are emitted toward the optical fiber FB4b.

Thereafter, the reflected light beam L3a and the reference light beam L2a enter a branching means 401a via the circulator 15a and an optical fiber 41a. The branching means 401a is constituted by a 2×2 optical coupler having a 50:50 branching ratio, for example. Approximately 50% of the reflected light beam L3a and the reference light beam L2a that enter the branching means 401a is emitted toward an optical fiber FB42a, and propagate therethrough to the combining means 4a. The remaining approximately 50% of the reflected light beam L3a and the reference light beam L2a that enter the branching means 401a is emitted toward an optical fiber FB43a, and enter the combining means 4a after the optical path length thereof is changed by the optical path length adjusting means 20a.

The interference light beam L4a is generated at the combining means 4a, by combining the reference light beam L2a, which has propagated thereto via the optical fiber FB42a, with the reflected light beam L3a, which has propagated thereto via the optical fiber FB43a, or by combining the reflected light beam L3a, which has propagated thereto via the optical fiber FB42a, with the reference light beam L2a, which has propagated thereto via the optical fiber FB43a. The interference light beam L4a is split into two light beams and emitted toward the interference light detecting means 40a.

Similarly, the reflected light beam L3b and the reference light beam L2b emitted toward the optical fiber FB4b enter a branching means 401b via the circulator 15b and an optical fiber 41b. The branching means 401b is constituted by a 2×2 optical coupler having a 50:50 branching ratio, for example. Approximately 50% of the reflected light beam L3b and the reference light beam L2b that enter the branching means 401b is emitted toward an optical fiber FB42b, and propagate therethrough to the combining means 4b. The remaining approximately 50% of the reflected light beam L3b and the reference light beam L2b that enter the branching means 401b is emitted toward an optical fiber FB43b, and enter the combining means 4b after the optical path length thereof is changed by the optical path length adjusting means 20b.

The interference light beam L4b is generated at the combining means 4b, by combining the reference light beam L2b, which has propagated thereto via the optical fiber FB42b, with the reflected light beam L3b, which has propagated thereto via the optical fiber FB43b, or by combining the reflected light beam L3b, which has propagated thereto via the optical fiber FB42b, with the reference light beam L2b, which has propagated thereto via the optical fiber FB43b. The interference light beam L4b is split into two light beams and emitted toward the interference light detecting means 40b.

The structures and operations of the interference light detecting means 40a, 40b, and the tomographic image processing means 50 are the same as those of the first embodiment, and therefore further descriptions thereof will be omitted.

Figure 13:
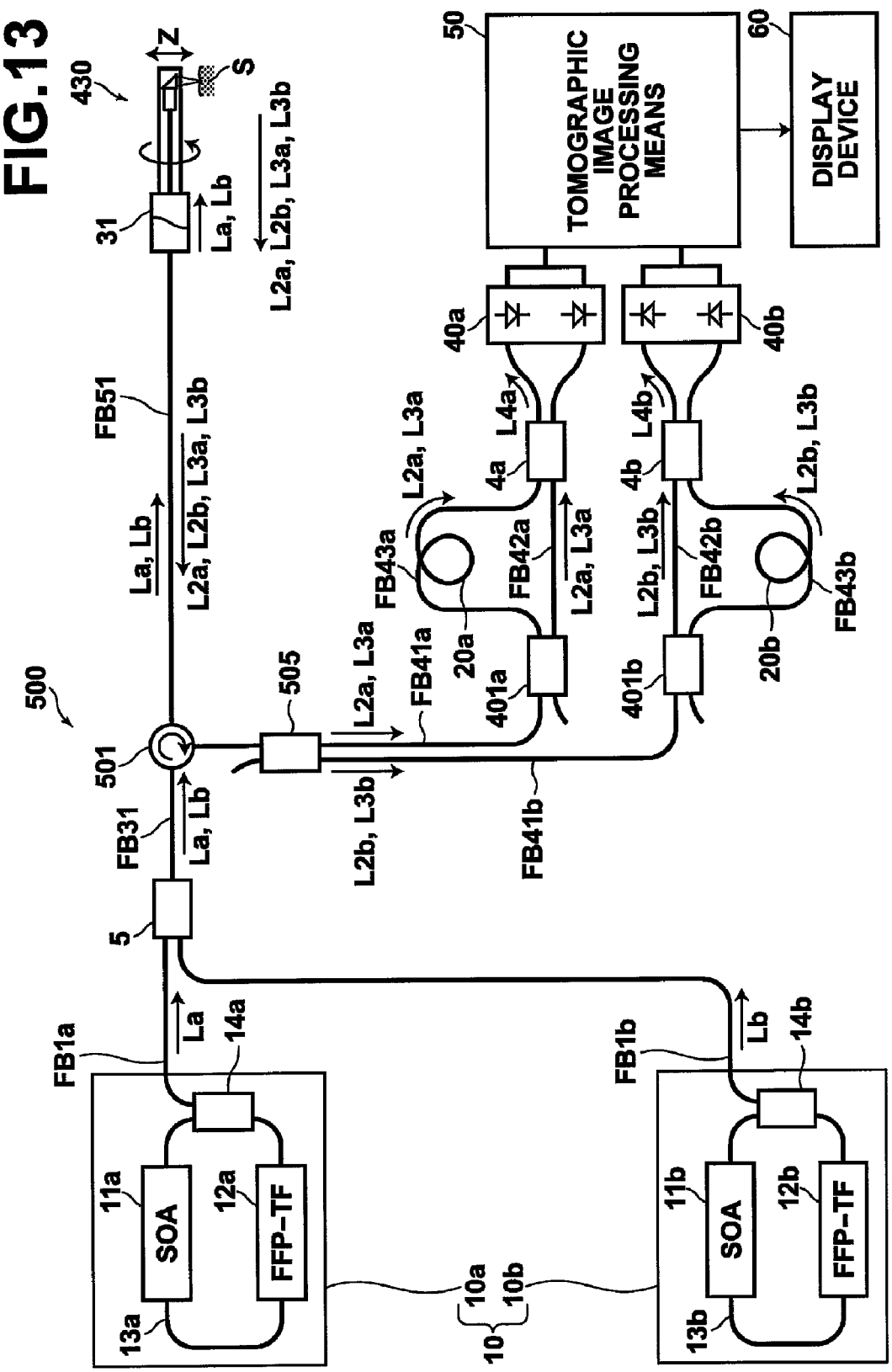
FIG. 13 is a diagram that illustrates the schematic construction of an optical tomograph according to a fifth embodiment of the present invention.

Next, an optical tomograph 500 according to a fifth embodiment of the present invention will be described with reference to FIG. 13. FIG. 13 is a diagram that illustrates the schematic construction of the optical tomograph 500. Note that in FIG. 13, components of the optical tomograph 500 which are the same as those of the optical tomographs of the previous embodiments are denoted with the same reference numerals, and that detailed descriptions thereof will be omitted, insofar as they are not particularly necessary. The optical tomograph 500 is an SS-OCT apparatus that employs a Fizeau interferometer. The optical tomograph 500 differs from the optical tomograph 400 in that the combining/dividing means 5 is provided upstream of the interferometer. Hereinafter, a description will be given mainly regarding the differences between the optical tomograph 500 and the optical tomograph 400.

In the optical tomograph 500, the light beam La emitted by the light source 10a propagates through the optical fiber FB1a, and enters the combining/dividing means 5. The light beam Lb emitted by the light source 10b propagates through the optical fiber FB1b, and enters the combining/dividing means 5. The combining/dividing means 5 combines the light beams La and Lb, and the combined light beam enters the probe 430 via an optical fiber FB51 and the rotary optical connector 31. The light dividing means 431 provided at the light emitting end of the probe 430 transmits a portion of the light beams La, Lb as measuring light beams L1a, L1b, and the remaining portion is reflected as reference light beams L2a, L2b. The measuring light beams L1a, L1b are irradiated onto the measurement target S, and the reflected light beams L3a, L3b are generated by the measuring light beams L1a, L1b being reflected by the measurement target S. The reflected light beams L3a, L3b, and the reference light beams L2a, L2b enter a light dividing means 505 via the probe 430, the optical fiber FB51, and a circulator 501.

The light dividing means 505 has wavelength selectivity, and is constituted by a WDM coupler, for example. The light dividing means 505 emits the reflected light beam L3a and the reference light beam L2a toward an optical fiber FB41a, and emits the reflected light beam L3b and the reference light beam L2b toward an optical fiber FB41b. The branching means 401a is linked to the optical fiber FB41a, and the branching means 401b is linked to the optical fiber FB41b. The operations which are performed at the branching means 401a, 401b and thereafter are the same as those which are performed by the fourth embodiment, and therefore further descriptions thereof will be omitted.

Figure 14:
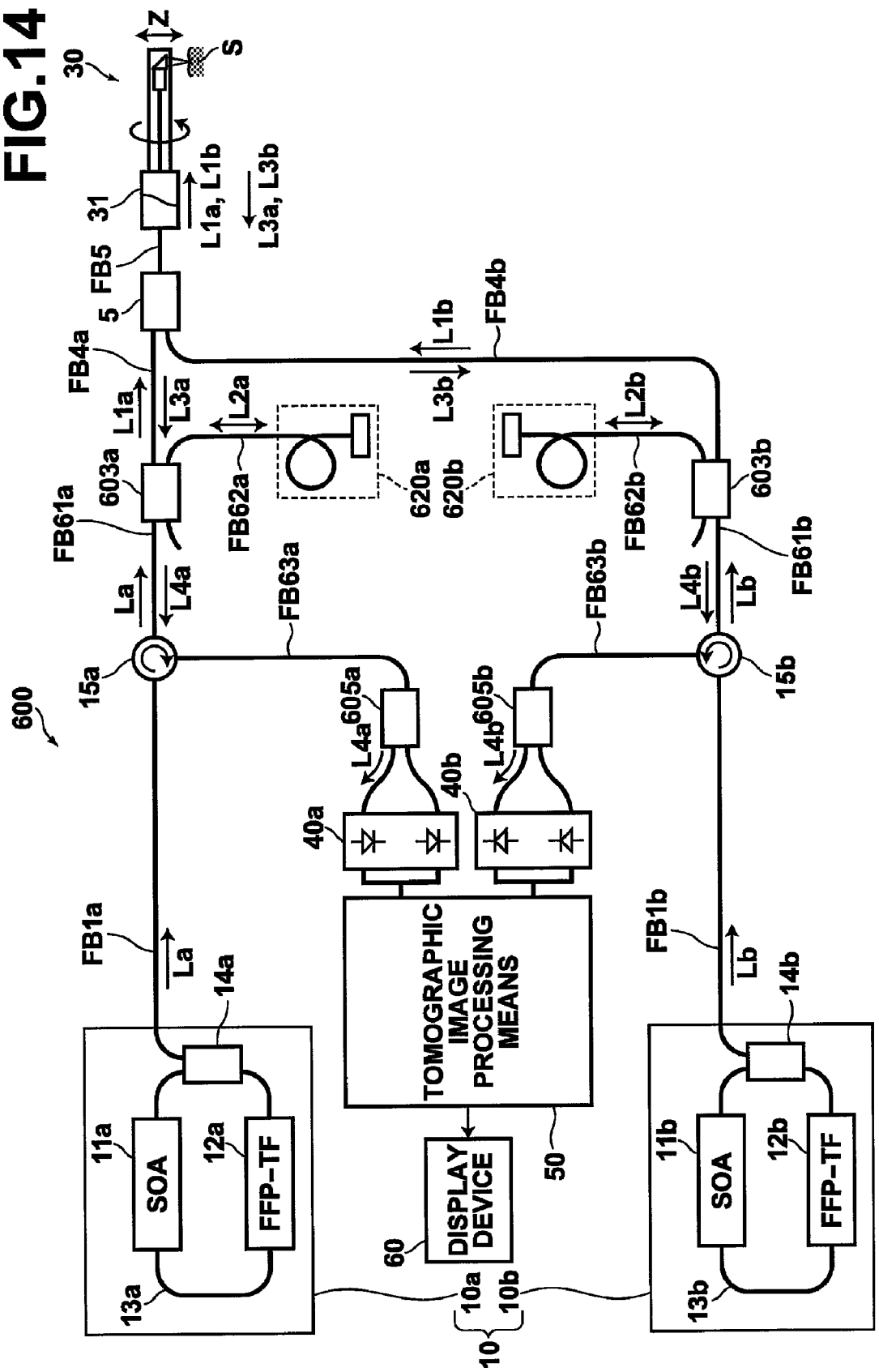
FIG. 14 is a diagram that illustrates the schematic construction of an optical tomograph according to a sixth embodiment of the present invention.

Next, an optical tomograph 600 according to a sixth embodiment of the present invention will be described with reference to FIG. 14. FIG. 14 is a diagram that illustrates the schematic construction of the optical tomograph 600. Note that in FIG. 14, components of the optical tomograph 600 which are the same as those of the optical tomographs of the previous embodiments are denoted with the same reference numerals, and that detailed descriptions thereof will be omitted, insofar as they are not particularly necessary. The optical tomograph 600 is an SS-OCT apparatus that employs a Michelson interferometer. In the optical tomograph 600, the light beam La, which is emitted by the light source 10a, enters a light dividing means 603a via the circulator 15a and an optical fiber FB61a. The light dividing means 603a is constituted by a 2×2 optical fiber coupler with a division ratio of 90:10, for example. Note that in the present embodiment, the light dividing means 603a also functions as a combining means. The light dividing means 603a divides the light beam La such that the ratio between the measuring light beam L1a and the reference light beam L2a becomes 90:10. The measuring light beam L1a is emitted toward the optical fiber FB4a, and the reference light beam L2a is emitted toward an optical fiber FB62a. The measuring light beam L1a propagates through the optical fiber FB4a and enters the combining/dividing means 5.

Similarly, the light beam Lb, which is emitted by the light source 10b, enters a light dividing means 603b via the circulator 15b and an optical fiber FB61b. The light dividing means 603b is constituted by a 2×2 optical fiber coupler with a division ratio of 90:10, for example. Note that in the present embodiment, the light dividing means 603b also functions as a combining means. The light dividing means 603b divides the light beam La such that the ratio between the measuring light beam L1b and the reference light beam L2b becomes 90:10. The measuring light beam L1b is emitted toward the optical fiber FB4b, and the reference light beam L2b is emitted toward an optical fiber 62b. The measuring light beam L1b propagates through the optical fiber FB4b and enters the combining/dividing means 5.

The combining/dividing means 5 combines the measuring light beams L1a and L1b, and the combined light beam enters the probe 30 via the optical fiber FB5 and the optical rotary connector 31. The combined measuring light beams L1a, L1b are irradiated onto the measurement target S, and the reflected light beams L3a, L3b reflected thereby enter the probe 30, then enter the combining/dividing means 5 via a route reverse to that through which the measuring light beams L1a and L1b propagated. The combining/dividing means divides the reflected light beam L3a and the reflected light beam L3b. The reflected light beam L3a is emitted toward the optical fiber FB4a and enters the light dividing means 603a. The reflected light beam L3b is emitted toward the optical fiber FB4b and enters the light dividing means 603b.

Meanwhile, the reference light beam L2a enters the light dividing means 603a via an optical fiber FB62a, after the optical path length thereof is adjusted by a reflective optical path length adjusting means 620a, which is connected to an end of the optical fiber FB62a. Similarly, the reference light beam L2b enters the light dividing means 603b via an optical fiber 62b, after the optical path length thereof is adjusted by a reflective optical path length adjusting means 620b, which is connected to an end of the optical fiber FB62b.

The reflected light beam L3a and the reference light beam L2a are combined at the light dividing means 603a. The interference light beam L4a generated thereby enters a branching means 605a via the optical fiber FB61a, the circulator 15a, and an optical fiber 63a. The branching means 605a is constituted by a 2×2 optical coupler having a 50:50 branching ratio, for example. The interference light beam L4a is split into two light beams by the branching means 605a, and emitted toward the interference light detecting means 40a.

Similarly, the reflected light beam L3b and the reference light beam L2b are combined at the light dividing means 603b. The interference light beam L4b generated thereby enters a branching means 605b via the optical fiber FB61b, the circulator 15b, and an optical fiber 63b. The branching means 605b is constituted by a 2×2 optical coupler having a 50:50 branching ratio, for example. The interference light beam L4b is split into two light beams by the branching means 605b, and emitted toward the interference light detecting means 40b.

The structures and operations of the interference light detecting means 40a, 40b, and the tomographic image processing means 50 are the same as those of the first embodiment, and therefore further descriptions thereof will be omitted.

Figure 15:
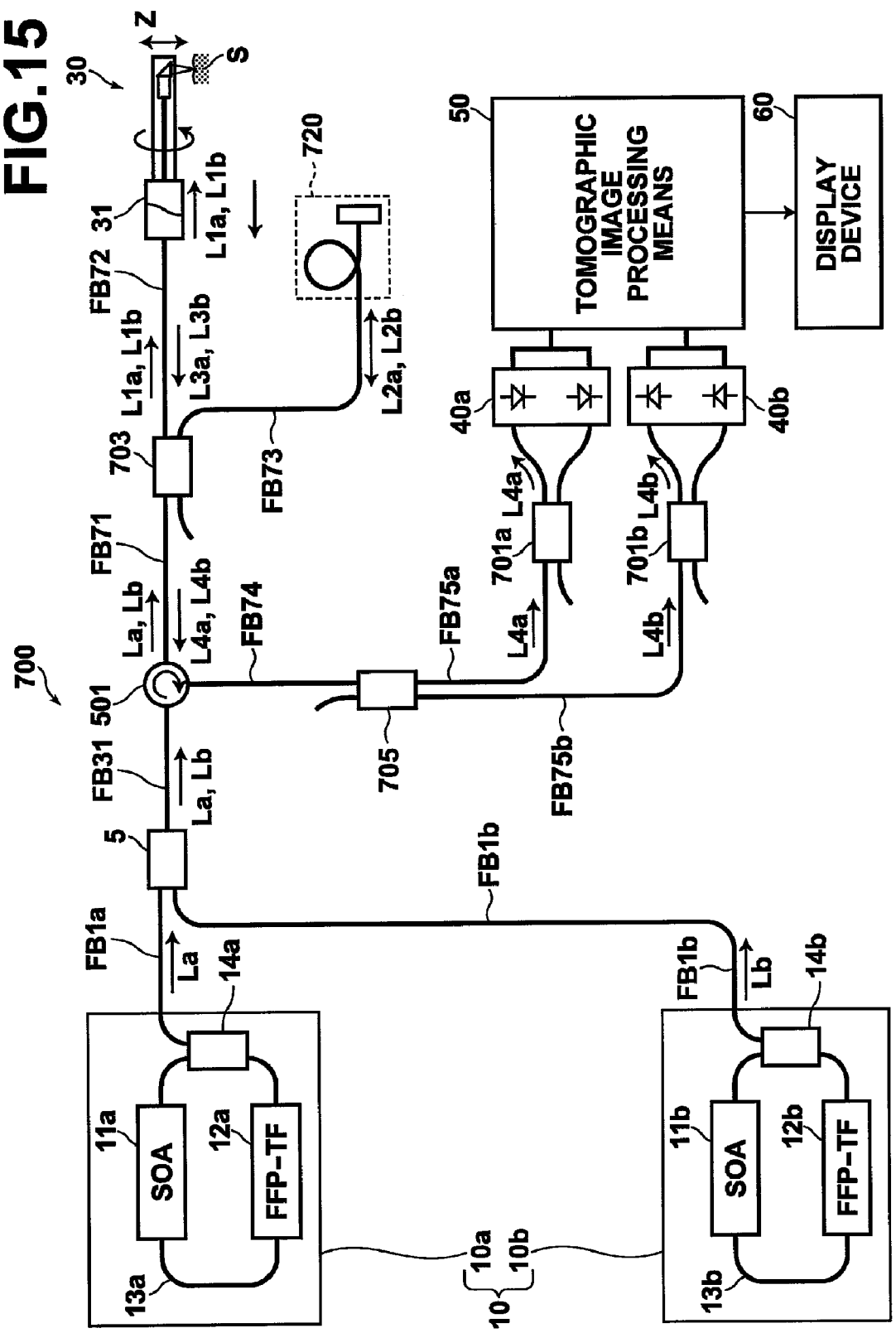
FIG. 15 is a diagram that illustrates the schematic construction of an optical tomograph according to a seventh embodiment of the present invention.

Next, an optical tomograph 700 according to a seventh embodiment of the present invention will be described with reference to FIG. 15. FIG. 15 is a diagram that illustrates the schematic construction of the optical tomograph 700. Note that in FIG. 15, components of the optical tomograph 500 which are the same as those of the optical tomographs of the previous embodiments are denoted with the same reference numerals, and that detailed descriptions thereof will be omitted, insofar as they are not particularly necessary. The optical tomograph 700 is an SS-OCT apparatus that employs a Michelson interferometer. The optical tomograph 700 differs from the optical tomograph 600 in that the combining/dividing means 5 is provided upstream of the interferometer. Hereinafter, a description will be given mainly regarding the differences between the optical tomograph 700 and the optical tomograph 600.

In the optical tomograph 700, the light beam La emitted by the light source 10a propagates through the optical fiber FB1a, and enters the combining/dividing means 5. The light beam Lb emitted by the light source 10b propagates through the optical fiber FB1b, and enters the combining/dividing means 5. The combining/dividing means 5 combines the light beams La and Lb, and the combined light beam enters a light dividing means 703 via the optical fiber FB31, the circulator 501, and an optical fiber FB71.

The light dividing means 703 is constituted by a 2×2 optical fiber coupler with a division ratio of 90:10, for example. Note that in the present embodiment, the light dividing means 703 also functions as a combining means. The light dividing means 703 divides the light beams La and Lb such that the ratios between the measuring light beams L1a, L1b and the reference light beams L2a, L2b become 90:10. The measuring light beams L1a, L1b are emitted toward an optical fiber FB72, and the reference light beams L2a, L2b are emitted toward an optical fiber FB73.

The measuring light beams L1a and L1b enter the probe 30 via the optical rotary connector 31, and are irradiated onto the measurement target S. The reflected light beams L3a, L3b reflected by the measurement target S enter the probe 30, and are guided to the light dividing means 703 via the probe 30 and the optical fiber FB72.

Meanwhile, the reference light beams L2a and L2b enter the light dividing means 703 via the optical fiber FB73, after the optical path length thereof is adjusted by a reflective optical path length adjusting means 720, which is connected to an end of the optical fiber FB73.

The reflected light beams L3a, L3b and the reference light beams L2a, L2b are combined at the light dividing means 703. The interference light beam L4a is generated by combining the reflected light beam L3a with the reference light beam L2a, and the interference light beam L4b is generated by combining the reflected light beam L3b with the reference light beam L2b. At this time, the wavelength bands of the light beams La and Lb are discrete, as illustrated in FIG. 2B. Therefore, no interference light beam is formed by a combination of the reflected light beam L3a and the reference light beam L2b or by a combination of the reflected light beam L3b and the reference light beam L2a.

The interference light beams L4a, L4b enter an interference light separating means 705 via the optical fiber FB71 and the circulator 501. The interference light separating means 705 has wavelength selectivity, and is constituted by a WDM coupler, for example. The interference light separating means 705 emits the interference light beam L4a toward an optical fiber FB75a, and emits the interference light beam L4b toward an optical fiber FB75b. A branching means 701a is linked to the optical fiber FB75a, and a branching means 701b is linked to the optical fiber FB75b. The branching means 701a and 701b are constituted by 2×2 optical couplers having division ratios of 50:50, for example. The interference light beams L4a and L4b are respectively split into two light beams by the branching means 701a and 701b, and are emitted toward the interference light detecting means 40a and 40b.

The structures and operations of the interference light detecting means 40a, 40b, and the tomographic image processing means 50 are the same as those of the first embodiment, and therefore further descriptions thereof will be omitted.

Figure 16:
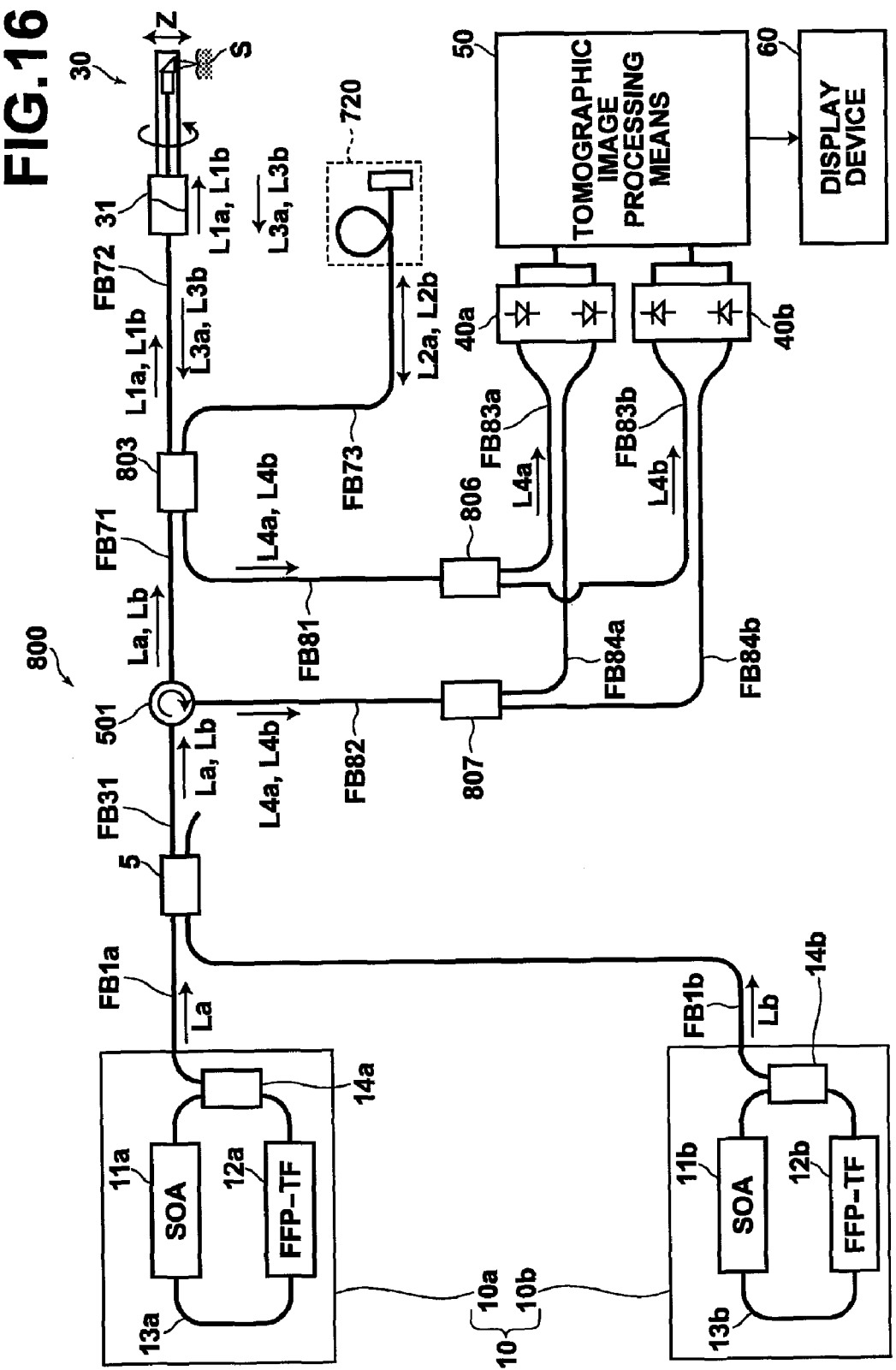
FIG. 16 is a diagram that illustrates the schematic construction of an optical tomograph according to an eighth embodiment of the present invention.

Next, an optical tomograph 800 according to an eight embodiment of the present invention will be described with reference to FIG. 16. FIG. 16 is a diagram that illustrates the schematic construction of the optical tomograph 800. The optical tomograph 800 is an SS-OCT apparatus that employs a Michelson interferometer. Note that in FIG. 16, components of the optical tomograph 800 which are the same as those of the optical tomographs of the previous embodiments are denoted with the same reference numerals, and that detailed descriptions thereof will be omitted, insofar as they are not particularly necessary.

The optical tomograph 800 comprises a light dividing means 803 instead of the light dividing means 703 of the optical tomograph 700. The light dividing means 803 is constituted by a 2×2 optical coupler having a division ratio of 50:50, for example. The operation of the optical tomograph 800 is the same as that of the optical tomograph 700, from emission of the light beams La, Lb by the light sources 10a, 10b, combination of the light beams La, Lb by the combining/dividing means 5, and guiding of the combined light beams via the circulator 501 and the optical fiber FB71.

Thereafter, the light beams La, Lb enter the light dividing means 803, and are divided into measuring light beams L1a, L1b and reference light beams L2a, L2b such that the ratio between the measuring light beams and the reference light beams becomes 50:50. The measuring light beams L1a, L1b are emitted toward the optical fiber FB72, and the reference light beams L2a, L2b are emitted toward the optical fiber FB73.

The measuring light beams L1a, L1b enter the probe 30 via the optical rotary connector 31, and are irradiated onto the measurement target S. The reflected light beams L3a, L3b reflected by the measurement target S enter the probe 30, and are guided to the light dividing means 803 via the probe 30 and the optical fiber FB72.

Meanwhile, the reference light beams L2a and L2b enter the light dividing means 803 via the optical fiber FB73, after the optical path length thereof is adjusted by the reflective optical path length adjusting means 720, which is connected to an end of the optical fiber FB73.

The reflected light beams L3a, L3b and the reference light beams L2a, L2b are combined at the light dividing means 803. The interference light beam L4a is generated by combining the reflected light beam L3a with the reference light beam L2a, and the interference light beam L4b is generated by combining the reflected light beam L3b with the reference light beam L2b. Approximately 50% of the interference light beams L4a, L4b is emitted toward an optical fiber FB81, and enter an interference light separating means 806. The remaining approximately 50% of the interference light beams L4a, L4b is emitted toward an optical fiber FB82, and enter an interference light separating means 807.

The interference light separating means 806 and 807 have wavelength selectivity, and are constituted by WDM couplers, for example. The interference light separating means 806 emits the interference light beam L4a toward an optical fiber FB83a, and emits the interference light beam L4b toward an optical fiber FB83b. The interference light separating means 807 emits the interference light beam L4a toward an optical fiber FB84a, and emits the interference light beam L4b toward an optical fiber FB84b. The interference light beam L4a propagates through the optical fibers FB83a, FB84a, and enters the interference light detecting means 40a. The interference light beam L4b propagates through the optical fibers FB83b, FB84b, and enters the interference light detecting means 40b.

The structures and operations of the interference light detecting means 40a, 40b, and the tomographic image processing means 50 are the same as those of the first embodiment, and therefore further descriptions thereof will be omitted.

Note that in the case that Michelson interferometers are employed to divide the light beams into measuring light beams and reference light beams at a 50:50 ratio as in the optical tomograph 800 as well, it is possible to provide the combining/dividing means 5 downstream of the interferometers, as in the optical tomograph 600 of FIG. 14.

In the first through eighth embodiments and the modification described above, the central wavelength $\lambda 1$ of the light beam La is 880 nm, and the central wavelength $\lambda 2$ of the light beam Lb is 1300 nm. In this case, Si photodiodes, which are capable of detecting light within a wavelength band of 320 nm to 1100 nm may be employed as the photodetecting elements of the interference light detecting means 40a, into which the light beam within the wavelength band $\Delta \lambda a$ enters. InGaAs photodiodes, which are capable of detecting light within a wavelength band of 900 nm to 1700 nm may be employed as the photodetecting elements of the interference light detecting means 40b, into which the light beam within the wavelength band $\Delta \lambda b$ enters.

Conventionally, OCT apparatuses were configured such that it was necessary for a single detector to be able to detect the entire wavelength range of light emitted from a light source unit. There are no photodiodes which are capable of detecting both of the wavelengths $\lambda 1$ and $\lambda 2$. Therefore, it had been impossible to construct an apparatus which is capable of measuring the combination of the wavelengths $\lambda 1$ and $\lambda 2$. However, the optical tomograph of the present invention is provided with a plurality of interference light detecting means, each for detecting a light beam corresponding thereto. Therefore, it is possible to measure the combination of the wavelengths $\lambda 1$ and $\lambda 2$. The light emitting process of semiconductor lasers which are employed in light sources and the photodetecting process of photodiodes which are employed in photodetectors are based on the same principle. Therefore, light within a wavelength band emitted by a semiconductor laser formed by a given medium is detectable by a photodiode formed by the same medium. Accordingly, by employing pairs of semiconductor lasers and photodiodes formed by the same material, all wavelength bands of light beams which are emitted can be measured.

In the case that the central wavelength $\lambda 1$ of the light beam La is 880 nm, and the central wavelength $\lambda 2$ of the light beam Lb is 1300 nm, it is desirable for optical tomographs that employ a plurality of interferometers, such as those illustrated in FIGS. 1, 7, 11, and 14, to utilize BIG ($Bi_3Fe_5O_{12}$) for the circulators 15a, into which light beams within the wavelength band $\Delta\lambda a$ enter, and to utilize YIG ($Y_3Fe_5O_{12}$) for the circulators 15b, into which light beams within the wavelength band $\Delta\lambda b$ enter. Conventionally, it had been necessary for a single circulator to circulate the entire wavelength range of light that circulated therethrough. Therefore, absorption loss was great in one of the wavelength bands, and there was a problem that the light utilization efficiency was poor. However, in the optical tomographs illustrated in FIGS. 1, 7, 11, and 14, interferometers are provided for each light beam, and therefore the above problem can be solved.

Alternatively, in the case that $\lambda 2$ is 1000 nm, TIG ($Tb_3Ga_5O_{12}$) may be utilized for the circulator 15b. Conventionally, it had been necessary for all optical components, such as circulators, couplers, dichroic mirrors, and optical fibers, to be able to handle all wavelength bands of light. In contrast, the optical components of the optical tomographs according to the embodiments of the present invention are only required to handle the wavelength band of each light beam. Therefore, constraints on the optical components that can be utilized are lessened, and the cost of components can be reduced.

Note that the optical tomograph of the present invention is not limited to using the wavelength bands described above. The wavelength bands to be utilized can be changed appropriately, according to the composition of the measurement target S. For example, a light beam within a wavelength band that has little interaction with the measurement target S (for example, the 1000 nm band, in which the influence of scattering by water is small) and a light beam within a wavelength band that has great interaction with the measurement target S (for example, the 800 nm band) may be combined. In this case, high resolution tomographic image data can be obtained, while spectral data regarding the measurement target, such as the absorption properties, the scattering properties, and the fluorescent properties, can also be measured.

In the case that the optical tomograph of the present invention is applied to an endoscope, a light beam having a central wavelength of 850 nm, which is within the sensitivity range of a CCD mounted within the endoscope, may be employed. In this case, the light beam may also function as an aiming light beam, and the need to provide a separate aiming light source is obviated.

The two light beams emitted by the light source units of the optical tomographs according to the first and third through eighth embodiments of the present invention have discrete wavelength bands. In conventional OCT apparatuses, it is considered ideal for the light sources to be used therein to emit light having a Gaussian spectrum. Side lobes become prominent in TD-OCT measurement, when a light source that emits light having a spectral shape other than a Gaussian shape is employed, which causes a problem that the resolution of tomographic images obtained thereby deteriorates. Meanwhile, in FD-OCT measurement, in which spectral signals are measured, the spectrum of the light emitted by the light source is measured in advance. Then, filter functions obtained from the measured spectrum are applied to the interference signals, to approximate signals obtained from light having a Gaussian distribution. However, it is necessary for the spectrum of light corresponding to a depth range, from which tomographic images are to be obtained, to be continuous. Appropriate processing cannot be administered onto discrete spectral shapes that have light intensities of 0 at the center of a light emission band, for example.

In addition, in conventional OCT apparatuses, it is desirable for the wavelength bands of light sources to be wide, in order to realize high resolution measurement. It is desirable from the viewpoint of cost to use inexpensive semiconductor light sources such as SLD's (Super Luminescent Diodes) or SOA's (Semiconductor Optical Amplifiers). However, the gain bands of these light sources are limited according to the medium properties thereof, and it is difficult to realize continuous bandwidths that exceed 100 nm using these light sources by themselves.

Therefore, methods, such as that disclosed in aforementioned Japanese Unexamined Patent Publication No. 2002-214125 are employed to widen the spectral width of light beams, by using a plurality of light sources, and integrating the light beams emitted from the plurality of light sources, have been proposed. Among these proposed methods, there are those in which optical couplers having 50:50 division ratios are employed to combine the light beams emitted from the plurality of light sources. However, the output of the light beam emitted from the optical coupler is half the total output of the combined light beams, and therefore the light utilization efficiency deteriorates. There are also methods that employ polarizing beam splitters to combine light beams. However, the number of light beams that can be combined using these methods is limited to two.

That is, in the Fourier transform method of OCT measurement, it is necessary for the spectrum of light emitted from a light source to be continuous and wide. Therefore, it had heretofore been considered that a light source unit that emits discrete light beams is not suited as a light source to be employed to obtain tomographic images in conventional OCT apparatuses.

However, as described in the first embodiment of the present invention, it is possible to obtain high resolution tomographic images using the light source unit 10 that emits light beams La and Lb having discrete wavelength bands, instead of a light source that emits light having a wide wavelength band. For this reason, the need to employ light source units which are to have the aforementioned specific properties is obviated. Further, the tomographic image processing means 50 generates the tomographic image from the pluralities of pieces of intermediate tomographic data. Accordingly, high resolution tomographic images without side lobes can be obtained, even though the light source unit that emits light having discrete spectra is employed.

Note that the optical tomographs of the first through eighth embodiments and the modification described above are all SS-OCT apparatuses. As described previously, SS-OCT apparatuses are advantageous in that the measurement rates thereof are faster than those of SD-OCT apparatuses. As a specific example, an OCT apparatus having a wavelength band of 200 nm and a wavelength resolution of 0.1 nm is considered. In order to obtain a high resolution, high quality tomographic image using this OCT apparatus, 2000 or more data points are necessary, and 4000 or more data points are desirable to obtain a more accurate spectral shape. It is also desirable for the OCT apparatus to perform video display of two dimensional tomographic images. In the case that images, in which the number of data points within the measurement wavelength band is 2000 and the number of lines in a direction perpendicular to the optical axis is 1000, are to be displayed at 10 Hz, a data readout rate of 20 MHz is necessary.

As described previously, in SD-OCT apparatuses, it is necessary to increase the number of photodetecting elements in order to increase the number of data points. An example of a currently available InGaAs element detector array, which is capable of detecting light within the near infrared range commonly used in OCT apparatuses, is SU-LDV-1024LE by Sensors Unlimited, Inc., which has 1024 elements. However, this detector array is expensive. In order to obtain 2000 data points or greater, or 4000 data points or greater, it is necessary to connect at least two and preferably four of these expensive 1024 element detector arrays. When a plurality of detector arrays are to be connected, highly accurate positional adjustment becomes necessary. Further, when the specifications of the aforementioned 1024 element detector array and a 512 element detector array (SU-LDV-512LD by Sensors Unlimited, Inc.), the maximum line rate is 12820 frames/sec for the 512 element detector array and 4266 frames/sec for the 1024 element detector array. That is, as the number of elements increases, the line readout rate decreases. The decrease in line readout rate leads to a decrease in the frame rate of images, which is a problem.

In contrast, in SS-OCT apparatuses, the number of data points can be increased inexpensively, simply by increasing the sampling rate of the detector. In the aforementioned example, 1000 line images can be displayed at 10 Hz, by obtaining data at a sampling rate of 40 MHz, even when the number of data points is 4000. This sampling rate is capable of being realized with photodiodes and an inexpensive electric circuit.

In addition, if the wavelength band of the measuring light beam is to be widened in an SD-OCT apparatus, changes in optical component design, such as wavelength dispersion elements (gratings) and focusing elements (lenses) become necessary. In contrast, in SS-OCT apparatuses, it is only necessary to provide additional WDM couplers and detectors. Therefore, widening of the wavelength band of the measuring light beam is facilitated in SS-OCT apparatuses.

Note that the present invention is not limited to the embodiments described above. Various changes and modifications are possible as long as they do not stray from the spirit of the invention. For example, a single light beam is emitted from each gain medium in the embodiments described above. Alternatively, multi color light sources that emit a plurality of light beams having different wavelengths from a single gain medium can be employed. In this case, the light source units 10 of the optical tomographs illustrated in FIG. 9, FIG. 13, FIG. 15, and FIG. 16 may be replaced with multi color light sources.

Figure 17:
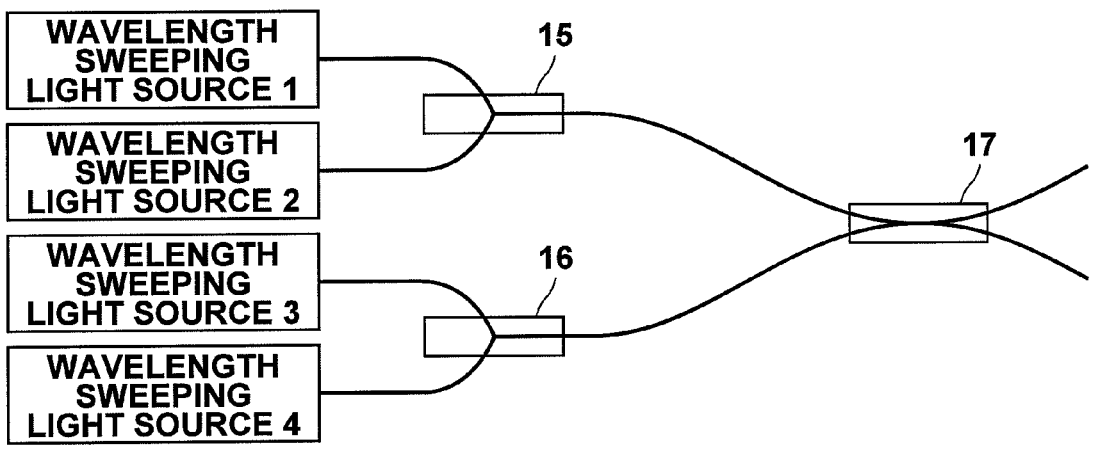
FIG. 17 is a diagram that illustrates an example of combining light beams from four light sources.
Figure 18:
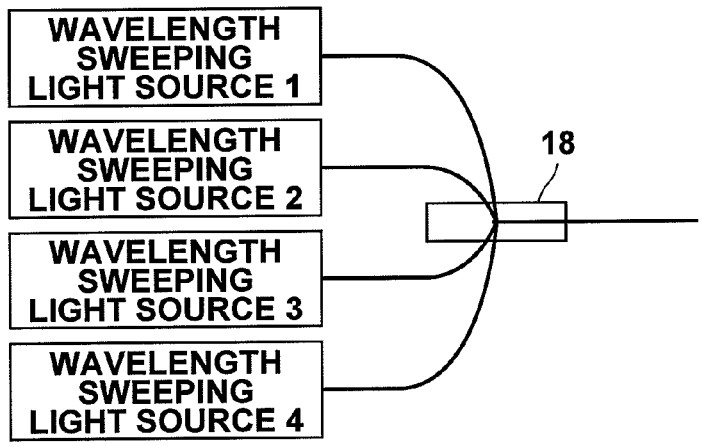
FIG. 18 is a diagram that illustrates another example of combining light beams from four light sources.

In the above embodiments, cases in which two light beams are employed were described to simplify the descriptions. However, the number of light beams may be three or greater. In the case that N number of light beams are employed, the OCT apparatus may comprise an N×1 WDM coupler or a plurality of WDM couplers. FIG. 17 illustrates a case in which four wavelength sweeping light sources 1, 2, 3, and 4 are employed. In this case, N=4, and two 2×1 WDM couplers 15, 16, ad a 2×2 WDM coupler 17 are employed to combine the light beams. FIG. 18 illustrates a case in which a single 4×1 WDM coupler 18 is employed to combine the light beams emitted from the four wavelength sweeping light sources 1, 2, 3, and 4.

Alternatively, the light sources disclosed in Japanese Unexamined Patent Publication No. 2006-047264 and U.S. Pat. No. 6,665,320 may be combined as a set, and light beams emitted by a plurality of sets may be combined.

In the above embodiments, fiber ring wavelength sweeping light sources were used as the light source units. However, other wavelength sweeping light sources may be employed. Examples of such light sources include those that employ diffraction gratings, polygon mirrors, and band pass filters as the wavelength selecting means, and those that employ rare earth ion doped fibers as gain media. Continuous wavelength sweeping is preferred, but discontinuous wavelength changes are also usable. The wavelength sweeping periods may be different for each light beam, unless they are synchronized as in the modification to the third embodiment.

In the above embodiments, the spectral shapes of each light beam emitted from the light source unit were substantially Gaussian spectra. However, the present invention is not limited to such a configuration, and the spectra may be those that have uniform intensities with respect to all wavelengths.

The light emitting wavelength bands of the light sources are not limited to the wavelength bands described in the above embodiments. However, it is necessary for the wavelength band of light emitted by the light source to be that which enables OCT measurement. There is no threshold value for a specific wavelength band, but in the case that a system is assumed that has a resolution on the order of 1 mm, the frequency band of the light is on the order of 10 GHz.

Optical fibers are employed to guide the light beams, and optical couplers and WDM couplers are employed to combine and divide the light beams in the embodiments described above. Alternatively, bulk optical systems that combine and divide light beams spatially, such as mirrors, prisms, dichroic mirrors, and dichroic prisms, may be employed. In addition, a configuration in which light beams which have propagated through space are scanned by a galvano mirror may be employed instead of the optical fiber probe.

The method by which mixing of interference signals and interference light beams is avoided when the wavelength bands of the light beams emitted by the light source unit overlap described in the second embodiment may be applied to the third through eighth embodiments as well.

In the above embodiments, light which is reflected or backscattered by the measurement target is measured. In the case that the measurement target is a transparent material, such as a glass block or a transparent film, transmitted light beams may be measured instead of the reflected light beams, in order to derive the planar refractive index distribution, the thickness distribution, and birefringence of the measurement target. In this case, the transmitted light is guided to the combining means and combined with the reference light beam. The other structures of the above embodiments may be applied without modifications thereto.

What is claimed is:

1. An optical tomograph, comprising:
   a light source unit for simultaneously emitting a plurality of light beams, the wavelengths of each of which are swept within different predetermined wavelength bands respectively;
   light dividing means, for dividing each of the light beams emitted from the light source unit into a measuring light beam and a reference light beam;
   combining means, for combining reflected light beams, which are the measuring light beams reflected by a measurement target when the measuring light beams are irradiated thereon, with the reference light beams divided by the light dividing means, for each of the light beams emitted by the light source unit;

interference light detecting means, for detecting an interference light beam, which is formed by the reflected light beam and the reference light beam being combined by the combining means, for each of the light beams as an interference signal; and tomographic image processing means, for generating a tomographic image of the measurement target employing the plurality of interference signals detected by the interference light detecting means, wherein:

a separate light dividing means and a separate combining means are provided for each of the light beams emitted from the light source unit.

2. An optical tomograph, comprising:

a light source unit for simultaneously emitting a plurality of light beams, the wavelengths of each of which are swept within different predetermined wavelength bands respectively;

light dividing means, for dividing each of the light beams emitted from the light source unit into a measuring light beam and a reference light beam;

combining means, for combining reflected light beams, which are the measuring light beams reflected by a measurement target when the measuring light beams are irradiated thereon, with the reference light beams divided by the light dividing means, for each of the light beams emitted by the light source unit;

interference light detecting means, for detecting an interference light beam, which is formed by the reflected light beam and the reference light beam being combined by the combining means, for each of the light beams as an interference signal; and tomographic image processing means, for generating a tomographic image of the measurement target employing the plurality of interference signals detected by the interference light detecting means, wherein:

at least two of the plurality of light beams emitted from the light source unit have wavelength bands that overlap; and the tomographic image processing means removes interference signals obtained based on the light of the overlapping wavelength band.

3. An optical tomograph as defined in claim 2, wherein:

a separate light dividing means and a separate combining means are provided for each of the light beams emitted from the light source unit.

4. An optical tomography as defined in claim 1, wherein:

at least two of the plurality of light beams emitted from the light source unit have discrete wavelength bands and continuous spectra within their respective wavelength bands;

the tomographic image processing means generates a tomographic image of a single portion of the measurement target, employing the interference signals obtained from the at least two light beams.

5. An optical tomography as defined in claim 1, wherein:

at least two of the plurality of light beams emitted from the light source unit have wavelength bands that overlap;

an optical filter for shielding light of the overlapping wavelength band is provided in the optical path between the light source unit and the interference light detecting means.

* * * * *